United States Patent [19]
Piwnica-Worms

[11] Patent Number: 5,863,729
[45] Date of Patent: Jan. 26, 1999

[54] DNA SEQUENCES ENCODING HUMAN TCAK1 KINASE

[75] Inventor: Helen Piwnica-Worms, Ladue, Mo.

[73] Assignee: Washington University, St. Louis, Mo.

[21] Appl. No.: 677,298

[22] Filed: Jul. 9, 1996

[51] Int. Cl.[6] .............................. C12Q 1/68; C07H 21/04; C12N 15/85

[52] U.S. Cl. ........................ 435/6; 435/240.1; 435/320.1; 536/23.1; 536/23.5; 536/24.31; 935/2; 935/6; 935/77; 935/78

[58] Field of Search ................................. 435/4, 6, 240.1, 435/320.1; 935/2, 9, 77, 78; 536/23.1, 23.2, 24.3, 24.31, 23.5

[56] References Cited

PUBLICATIONS

Ogg et al. (1994), "Purification of a Serine Kinase That Associates with and Phosphorylates Human Cdc25C on Serine 216," J. Biol. Chem. 269:30461–30469.
Ford et al. (1994), "14–3–3 Protein Homologs Required for the DNA Damage Checkpoint in Fission Yeast," Science 265:533–535.
Morrison (1994), "14–3–3: Modulators of Signaling Proteins?" Science 266:56–57.
Aitken (1995), "14–3–3 Proteins on the MAP," TIBS 20:3pp.
Muslin et al. (1996), "Interaction of 14–3–3 with Signaling Proteins is Mediated by the Recognition of Phosphoserine," Cell 84:889–897.
Accession M80359.
A Usubel et al Editors of Short Protocols In Molecular Biology. John Wiley & Sons, New York (1989) pp. 75–79, 106–116, and 158–159.
Sequence Alignment of p78 and Seq. ID Nos. 1 & 2.

Primary Examiner—W. Gary Jones
Assistant Examiner—Debra Shoemaker
Attorney, Agent, or Firm—Greenlee, Winner and Sullivan, P.C.

[57] ABSTRACT

Entry into mitosis requires the activity of the Cdc25C phosphatase which functions to activate Cdc2/Cyclin B. In asynchronously growing cells, Cdc25C is stoichiometrically phosphorylated on serine 216. Levels of serine 216 phosphorylation remain constant throughout the G1-, S- and G2-phases of the cell cycle. A human kinase, denoted TcAK1 (for Twenty-five C Associated protein Kinase) that phosphorylates Cdc25C on serine 216 has been cloned and sequenced. A method is also provided for measuring levels of TcAK1 in RNA or of TcAK1 protein in cells. Phosphorylation of Cdc25C on serine 216 with TCAK1 creates a 14-3-3 recognition motif. The interaction between Cdc25C and 14-3-3 proceeds in a phosphorylation-specific manner. TcAK1 functions to mediate interaction between 14-3-3 proteins and other cellular proteins associated with oncogenesis or key signalling events.

9 Claims, 15 Drawing Sheets

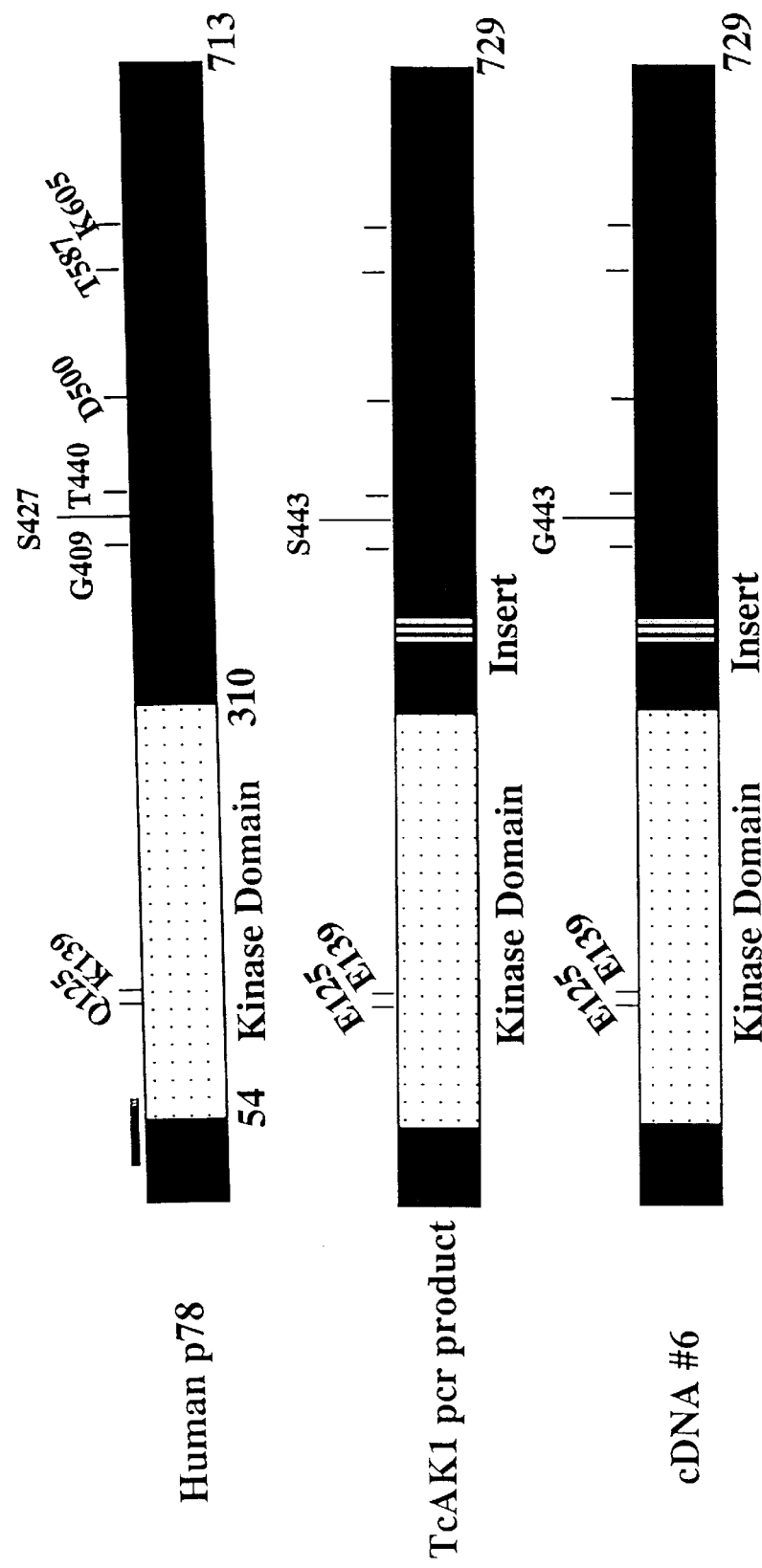

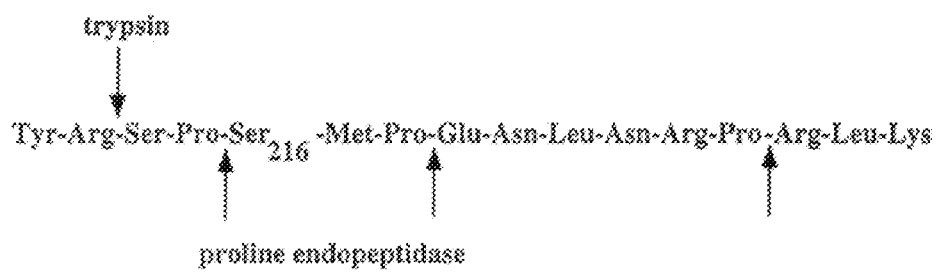
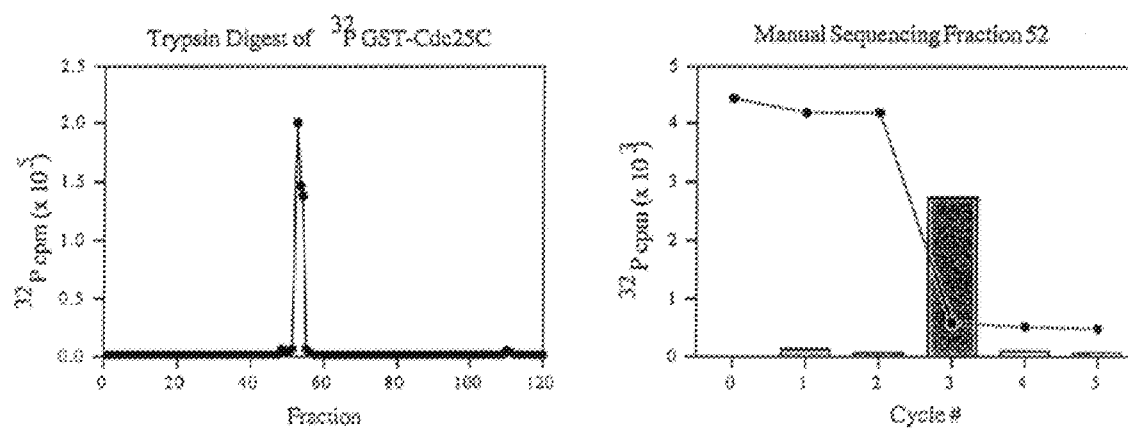
FIGURE 3B

5,863,729

DNA SEQUENCES ENCODING HUMAN TCAK1 KINASE

The U.S. Government has certain rights in the invention based upon research support provided by National Institutes of Health Grant No. GM 47017.

FIELD OF THE INVENTION

The invention relates to nucleotide sequences encoding a protein known to function in regulating cell division.

BACKGROUND OF THE INVENTION AND PRIOR ART

The cells of eukaryotes, including humans and other mammals, replicate themselves by carrying out an ordered sequence of events, which are cyclically repeated in each successive cell division. In somatic (non germ-line) cells, a typical cycle has four characterized phases: G1, an interval following the completion of mitosis, also termed first gap phase; S, a period during which the cell undergoes DNA synthesis; G2 or second gap phase following completion of DNA synthesis and preceding mitosis; and M, mitosis, where separation of complete sets of replicated DNA occurs. The end result of this process is the generation of two daughter cells that are equivalent both in genetic makeup and in size to the original parent cell. A complex series of biochemical interactions act to control the cell cycle through a series of checkpoints or gating reactions which function to ensure that the requisite precursor phases are completed before the ensuing phase begins. In particular, the checkpoints ensure accurate reproduction and dispersion of the cell's genetic material. In a metazoan organism with differentiated tissues, such as a human being, cells of different tissues replicate at vastly different rates at different life stages. Early embryonic cells replicate rapidly and synchronously, whereas at later stages of development and during adulthood, some cells, such as muscle and nerve cells stop replicating while others, such as epithelial cells, continue to divide throughout the organism's life. Failure of cells to precisely control their replicative state therefore leads to a variety of diseases of pathological proliferation, including cancers and atherosclerosis.

Progress over the past several years has greatly advanced the general understanding of the biochemical reactions which regulate the cell cycle. A general paradigm for cell cycle regulation has emerged in which complexes composed of cyclins and cyclin-dependent kinases (CDKs) regulate progression through stages of the cell cycle. Several mechanisms exist to keep the activity of the cyclin/CDK complexes turned off until the appropriate stage of the cell cycle. Known mechanisms include reversible phosphorylation, binding to small molecular weight inhibitors, transcription control, intracellular location and protein degradation. In yeast, there are multiple cyclins but only a single CDK. The CDK of fission yeast is encoded by the cdc2 gene, that of budding yeast by the cdc28 gene. In higher eukaryotes, including humans, there are multiple CDKs as well as multiple cyclins. Despite the greater complexity of the higher eukaryotes, the overall scheme for cell cycle progression involving cyclins and CDKs is conserved. Deregulation of components of these regulatory pathways has been implicated in human cancer. For a recent general review, see Hunter, T. et al. (1994) *Cell* 79:573–582.

In humans, there are three known Cdc25 phosphatases, denoted Cdc25A, Cdc25B and Cdc25C. Cdc25B has been shown to be overexpressed in certain breast cancers. In human cells, Cdc25C is present throughout the cell cycle. Its substrate, Cdc2/cyclin B, accumulates throughout the S and G2 phases of the cell cycle. Cdc25C is itself regulated by phosphorylation. The major site of Cdc25C phosphorylation is serine 216 (Ogg, S. et al. (1994) *J. Biol. Chem.* 269:30461–30469). The protein kinase that acts on Cdc25C was purified over 8000-fold from rat liver. [Ogg, S. et al. (1994) J. Biol. Chem. 269:30461.] It was shown to phosphorylate a peptide substrate having the sequence of amino acids 210–231 of human Cdc25C, but not the equivalent peptide in which serine 216 had been changed to a threonine. The kinase is referred to herein as TcAK1, an acronym for twenty-five C associating kinase.

A family of proteins known as 14-3-3 proteins was first identified by Moore, B. F. et al. (1967) as very abundant 27–30 kD acidic proteins of brain tissue (*Physiological and Biochemical Aspects of Nervous Integration*, F. D. Carlson, Ed., Prentice-Hall, Englewood Cliffs, N.J., 1967). Their name reflects the original investigators' nomenclature. Recent work has implicated the participation of 14-3-3 proteins in cell cycle control (Ford, J. C. et al. (1994) *Science* 265:533). (For a general review, see Morrison, D. (1994) *Science* 266:56–57 and Aitken, A. (1995) *TIBS* 20). A variety of functions have been ascribed to the 14-3-3 proteins. However, several lines of evidence suggest that they link signal transduction cascades with the cell cycle. Various 14-3-3 isoforms have been found in complexes with proteins that transform cells, e.g., the middle T antigen of polyoma virus and Bcr-Ab1, with signaling molecules, e.g., c-Raf1, c-Bcr and P13k, and with two cell cycle regulators, e.g., Cdc25A and CdcB. The ability of a protein to bind or form a complex with a 14-3-3 protein therefore indicates that the protein is a key element linking external or internal signal transduction with other cell functions. In the present invention that other function is the cell replication cycle, specifically passage from G2 to mitosis.

SUMMARY OF THE INVENTION

The CDNA (SEQ ID NO:1) of human TcAK1 kinase (SEQ ID NO:2), which phosphorylates Cdc25C on serine 216, has been cloned and sequenced. The invention provides isolated, purified and structurally defined DNA encoding human TcAK1, a method for making TcAK1 protein by expressing the DNA encoding TcAK1, novel fusion proteins having TcAK1 protein coupled to additional amino acids, and methods for measuring levels of TcAK1 in RNA or of TcAK1 protein in a cell sample. The invention also demonstrates that phosphorylation of human Cdc25C on serine 216 creates a 14-3-3 recognition motif and that TcAK1 plays a role in mediating interactions between Cdc25C and 14-3-3 proteins. In addition, TcAK1 also has a general function in mediating interactions between 14-3-3 proteins and other cellular proteins that play a key role in oncogenesis or key signalling events. Measurement of protein binding at TcAK1-mediated 14-3-3 recognition sites are therefore useful for detecting the presence of cancer or other disorder of cell proliferation.

BRIEF DESCRIPTION OF THE FIGURES

FIG. 1: Sequence obtained from rat p36TcAK1

A: Sequence of 25 amino acids obtained from purified rat TcAK1 (SEQ ID NO:3).

B: Schematic representation of human p78 (from database), TcAK1 PCR product and TcAK1 cDNA #6 (SEQ ID NO:1) clone.

Figure 2A:
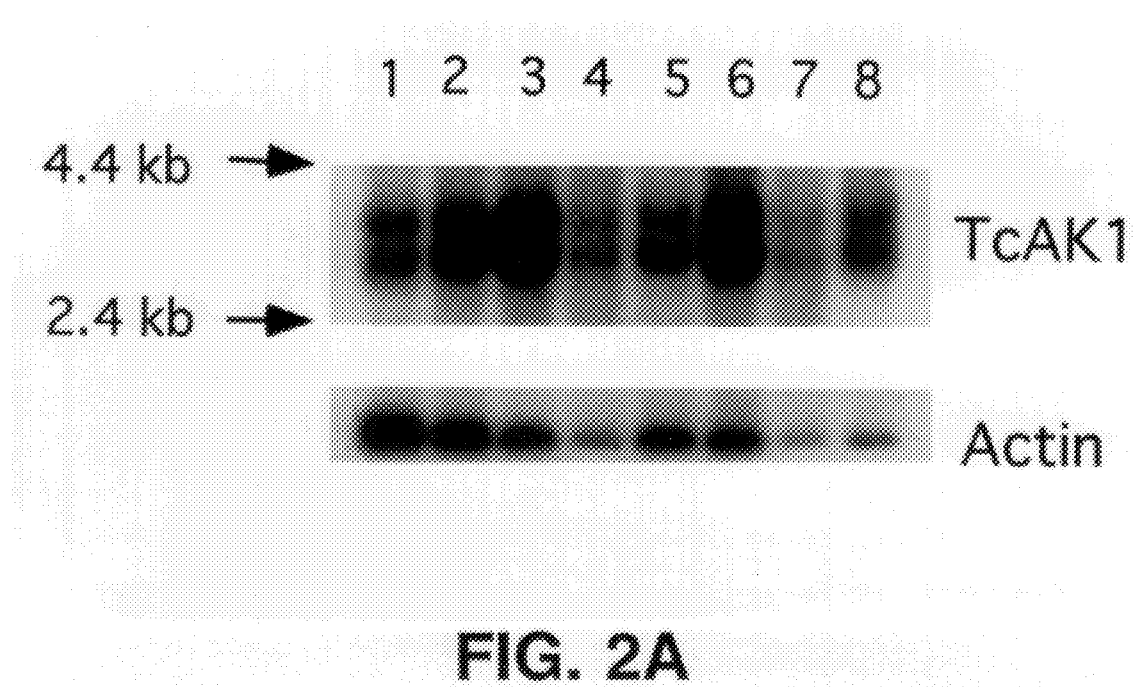

FIG. 2: Expression and activity of TcAK1

A: mRNA from the following human cancer cell lines was probed with radiolabeled human TcAK1 cDNA: promyelocytic leukemia HL-60 (lane 1); HeLa cell S3 (lane 2); chronic myelogenous leukemia K-562 (lane 3); lymphoblastic leukemia MOLT-4 (lane 4); Burkitt's lymphoma Raji (lane 5); colorectal adenocarcinoma SW480 (lane 6); lung carcinoma A549 (lane 7); melanoma G361 (lane 8). The human TcAK1 probe was stripped and the blot described above was hybridized with radiolabeled human B-actin probe (bottom).

B: Left Panel: Lysates prepared from HeLa (lane 1) and Jurkat cells (lanes 2) were resolved directly on an 8% SDS polyacrylamide gel. Proteins were transferred to nitrocellulose and incubated with TcAK1-specific antibodies. Proteins were visualized with an ECL Western blotting detection method. Right Panel: Lysates prepared from HeLa (lanes 1 and 2) and Jurkat cells (lane 3) were immunoprecipitated with either pre-immune sera (lane 1) or affinity purified TcAK1 antibodies (lanes 2, 3) prior to SDS-PAGE. TCAK1 was visualized as described in left panel.

C: TcAK1 (lane 1) and a mutant of TcAK1 (lane 2) where N183 was changed to alanine were produced in bacteria as His-tagged fusion proteins. Recombinant protein was isolated on Ni-NTA beads and kinase assays were performed in vitro (left). Radiolabeled His-TcAK1 was subjected to phosphoamino acid analysis (right).

FIG. 3: TcAK1 phosphorylates Cdc25C on serine 216 in vitro.

A. Kinase assays were performed in vitro in the presence of bacterially produced His-tagged TcAK1 and the following GST-fusion proteins purified from overproducing bacteria: GST-Cdc25C (lane 1) GST-Cdc25C(S216A) (lane 2), GST-N258 (lane 3) GST-N258(S216A) (lane 4). Reactions were resolved on a 7% gel and visualized by autoradiography.

B. Radiolabeled GST-Cdc25 fragment (SEQ ID NO:4) was digested with trypsin and the tryptic peptides were resolved by reverse phase HPLC (FIG. 3B-1). Column fractions were collected and monitored for the presence of radioactivity (FIG. 3B-2).

Manual Edman degradation of tryptic phosphopeptides present in fraction 52 (FIG. 3B-3).

C. The tryptic phosphopeptide from HPLC fraction 52 (above) was further digested with proline specific endopeptidase and reaction products were resolved by reverse phase HPLC (FIG. 3C-1). Manual Edman degradation of phosphopeptides present in fractions 18 (FIG. 3C-2) and 51 (FIG. 3C-3).

Figure 4A:
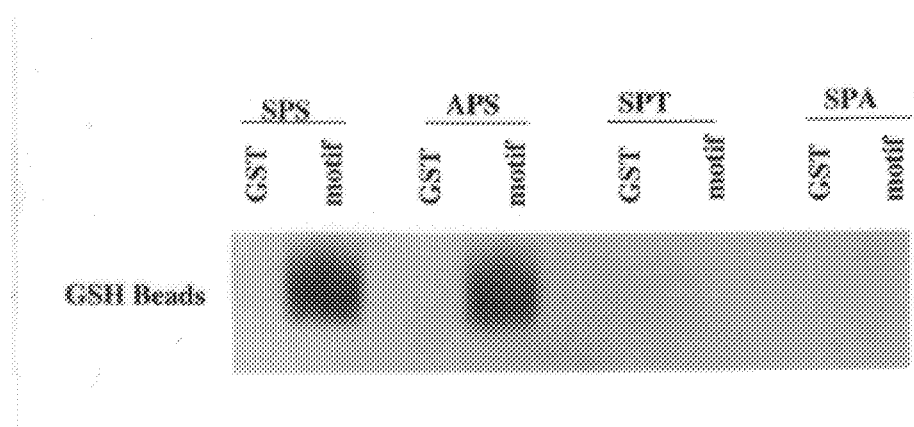
Figure 4B:
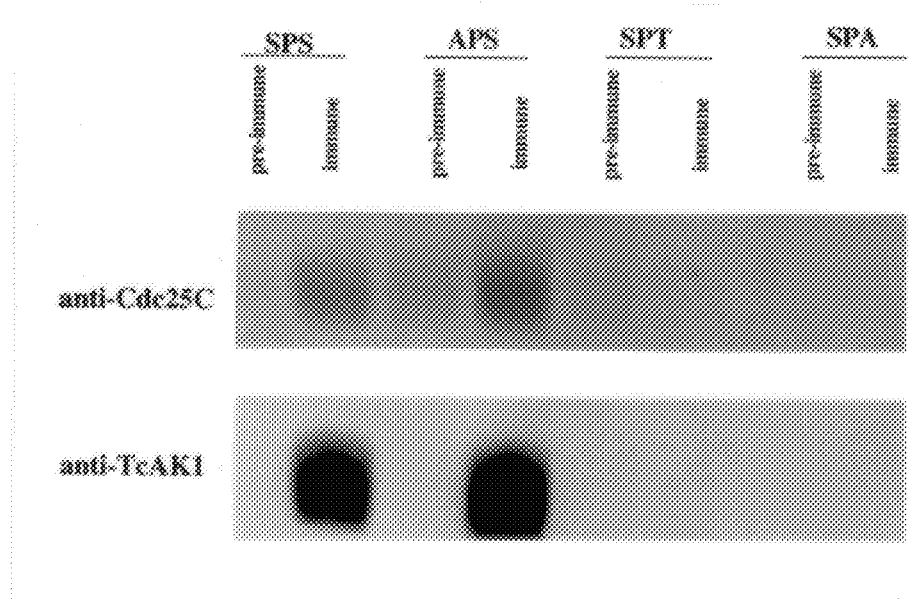

FIG. 4: Coprecipitation of Cdc25C and a kinase with the same substrate specificity as TcAK1.

A: Lysates prepared from HeLa cells were incubated with immobilized GST or GST-motif [Cdc25C(200–256)]. After washing, the beads were divided into four aliquots each and peptide kinase assays were performed in vitro. The peptides used correspond to amino acids 210–231 of human Cdc25C (SPS) or with substitutions of serine 214 with alanine (APS) or serine 216 with either alanine (SPA) or threonine (SPT). Phosphorylated peptides were resolved by SDS-PAGE and visualized by autoradiography.

B. Lysates prepared from HeLa cells were incubated with pre-immune sera, affinity purified TcAK1 antibodies (anti-TcAK1) or affinity purified Cdc25C antibodies (anti-Cdc25C). Immune complex kinase assays were performed in vitro in the presence of the Cdc25 peptides described in panel A above. Phosphorylated peptides were resolved by SDS-PAGE and visualized by autoradiography.

Figure 5A:
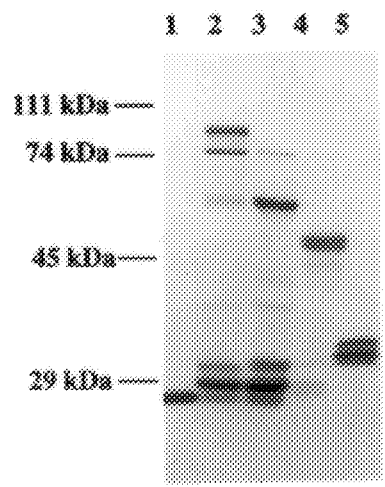

FIG. 5: Binding specificity of recombinant TcAK1

Figure 5B:
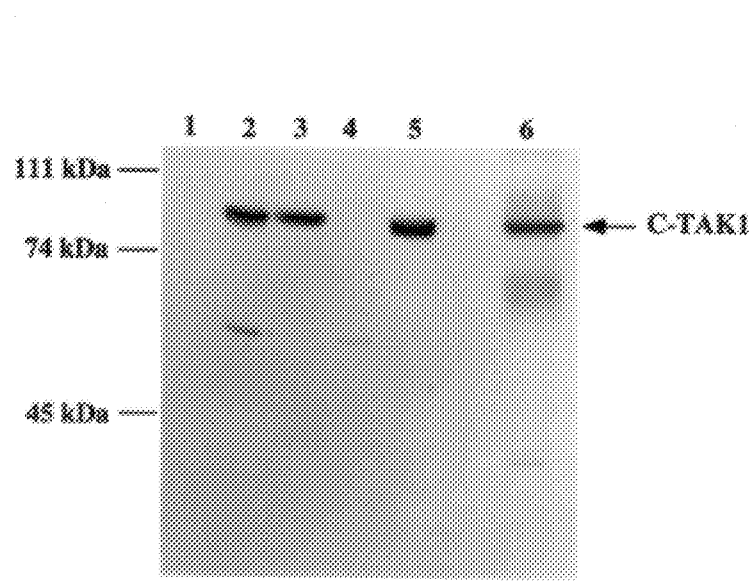

Lysates prepared from bacteria overproducing CST (lane 1), GST-Cdc25C (lane 2), GST-25C(N258) (lane 3), GST-25C(C215) (lane 4) or GST-25C motif (lane 5) were incubated with GSH-agarose beads. A portion of the beads were resolved on a 10% SDS gel followed by staining with Coomassie Blue (FIG. 5A) the remainder of the beads were incubated with lysates prepared from insect cells overproducing TcAK1. Beads were pelleted, washed, resolved on a 10% SDS gel, transferred to nitrocellulose and probed with TcAK1 antibody (FIG. 5B). TcAK1 was visualized using an ECL Western blot detection method. 15 µg of lysate prepared from TcAK1 expressing insect cells were resolved and analyzed by blotting as described above (lane 6).

Figure 6:
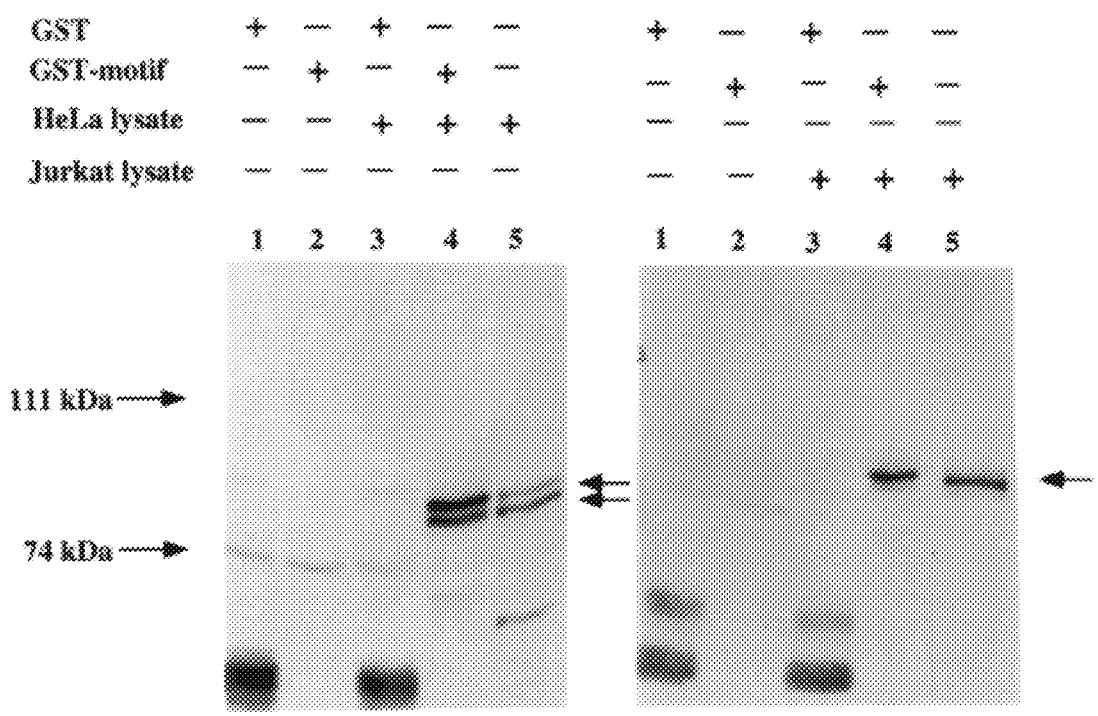

FIG. 6: Binding of Cdc25C motif to endogenous TcAK1

Lysates prepared from bacteria overproducing GST (lanes 1, 3) or GST-25C motif (lanes 2, 4) were incubated with GSH-agarose beads. Half of the beads were resolved directly on a 10% SDS gel (lanes 1, 2), the other half was incubated with lysates prepared from either HeLa (left panel) or Jurkat (right panel) cells prior to SDS-PAGE. Beads were pelleted, washed, resolved on a 10% SDS gel, transferred to nitrocellulose and probed with TcAK1 antibody. TcAK1 was visualized using an ECL Western blot detection method. 50 µg of total cellular lysate prepared from either HeLa (lane 5, left panel) or Jurkat cells (lane 5, right panel) were resolved and analyzed as described above.

FIG. 7: The majority of Cdc25C is phosphorylated on serine 216 in asynchronously growing HeLa cells.

A. Lysates were prepared from HeLa cells in the presence (lanes 1, 2) or absence (lane 3) of microcystin. Lysates were incubated with pre-immune sera (lane 1) or sera specific for Cdc25C (lanes 3, 4). Immunoprecipitates were resolved by SDS- PAGE and Cdc25C was detected by immunoblotting.

B. HeLa cells were transfected with vector alone (lane 1) vector encoding myc-tagged Cdc25C (lane 2) or vector encoding myc-tagged Cdc25C(S216A) (lane 3). At 20 hrs. after transfection, lysates were prepared, resolved by SDS-PAGE and immunoblotted for Cdc25C using a monoclonal antibody specific for the myc epitope sequence.

FIG. 8: Cell cycle regulation of serine 216 Phosphorylation, TcAK1 levels and TcAK1 activity.

A. Asynchronous or elutriated populations of Jurkat cells were lysed, resolved by SDS-PAGE and immunoblotted for Cdc25C. Cdc25C in asynchronous cells (lane 1); cells enriched in G1 (lane 2); cells enriched in S (lane 3); cell enriched in G2/M (lane 4).

B and C. Asynchronous (lanes 1, 2) or elutriated populations (lanes 3, 4, 5) of Jurkat cells were lysed and immunoprecipitated with either pre-immune sera (lane 1) or sera specific for TcAK1 (lanes 2, 3, 4, 5). Immunoprecipitates were divided in half. One half was resolved by SDS-PAGE and immunoblotted for TcAK1 (B). Immune complex kinase assays were performed with the second half of each reaction using the APS peptide as substrate (C). Reactions were resolved by SDS-PAGE and subjected to autoradiography. Asynchronous cells (lanes 1, 2); cells enriched in G1 (lane 3); cells enriched in S (lane 4); cell enriched in G2/M (lane 5).

Figure 9A:
Figure 9B:
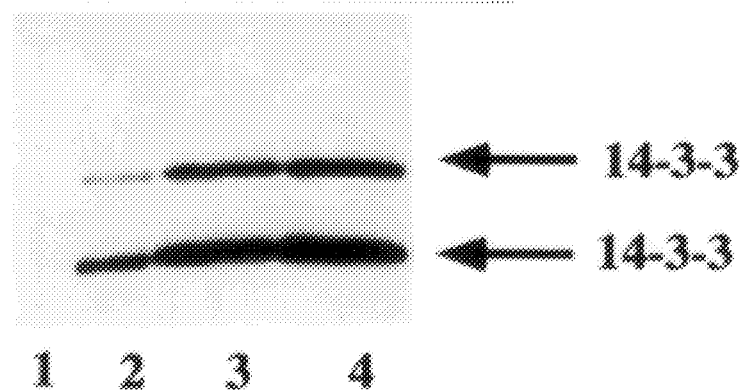

FIG. 9: Association between Cdc25C and 14-3-3 in insect cells.

Insect cells infected with recombinant baculoviruses encoding GST-C215 (lane 1); GST-N258 (lane 2); GST- Cdc25C (lane 3); or GST-Cdc25C(C377S) (lane 4) were lysed and incubated with GSH agarose beads. Precipitates were washed, resolved by SDS-PAGE, transferred to nitrocellulose and probed with either GST antibodies to visualize recombinant Cdc25C proteins (A) or with antibodies specific for 14-3-3 (B). Proteins were visualized using an ECL Western blot detection method.

FIG. 10: Association between Cdc25C and 14-3-3 in Hela cells requires serine 216.

HeLa cells were transfected with pcDNA3 lacking an insert (pcDNA3, lane 2) or with plasmids encoding either myc-epitope tagged Cdc25C (Myc-Cdc25C, lane 1) or myc-epitope tagged Cdc25CS216A [Myc-Cdc25C(S216A), lane 3]. Lysates were prepared and incubated with monoclonal antibodies to the myc epitope. One half of the immunoprecipitate was analyzed on an 8% polyacrylamide gel, transferred to nitrocellulose and blotted with the E10 monoclonal antibody to detect Cdc25C (A). Detection of bound secondary antibody (HRP-conjugated goat anti-mouse, Cappel) was achieved using Amersham's ECL kit. The other half of the sample was analyzed for activation of exoenzyme S activity (B).

FIG. 11: Association between endogenous Cdc25C and 14-3-3 in Hela Cells.

Immunoprecipitates were prepared from HeLa cell lysates using C20 antibody which was generated using a peptide derived from the carboxy-terminus of human Cdc25C (A, lanes 3, 4) or with antibody that was pre-incubated with the immunogenic peptide (A, lanes 1, 2). Half of the immunoprecipitate was immunoblotted for the presence of Cdc25C (A) and half was assayed for the activation of exoenzyme S activity (B).

Figure 12:
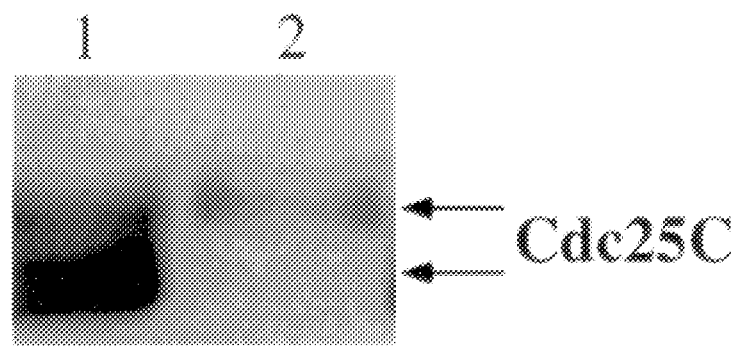

FIG. 12: Phosphorylation of Cdc25C on serine 216 creates a 14-3-3 recognition motif.

Insect cells overproducing Cdc25C were lysed and lysates were resolved directly by SDS-PAGE (lane 1). Alternatively, lysates were incubated with purified GST-14-3-3 and bound proteins were precipitated using GSH agarose. Precipitates were washed and resolved by SDS-PAGE (lane 2). Cdc25C was visualized by immunoblotting.

DETAILED DESCRIPTION OF THE INVENTION

Definitions—The following terms are defined herein for convenience and clarity in describing and claiming the invention.

The term kinase as used herein refers to an enzyme which catalyzes transfer of a phosphate group from a high energy form of phosphate, such as adenosine triphosphate (ATP) or guanosine triphosphate (GTP) to an acceptor group such as a hydroxyl. The acceptor is said to be phosphorylated. Protein kinases are enzymes which act to phosphorylate an acceptor group on a protein, notably a hydroxyl of serine, threonine or tyrosine. Many protein kinases are very specific in that the acceptor substrate can be one particular hydroxyl group on one particular protein. Some acceptor proteins become activated by phosphorylation, others inactivated. As noted for Cdc25C, phosphorylation at Ser 216 regulates its function, including providing a 14-3-3 binding site.

The term 14-3-3 protein(s) or 14-3-3 as used herein refers to a highly conserved multigene family of small (approximately 30 kDa) acidic proteins found in a wide variety of eukaryotic organisms. 14-3-3 proteins function as activators of tyrosine hydroxylase, as regulators of protein kinase C and as co-factors of the Pseudomonas toxin exoenzyme S. Various 14-3-3 isoforms have been found in complexes with oncogenes, signaling molecules and cell cycle regulators. Genetic studies implicate 14-3-3 proteins as negative regulators of mitosis. This 14-3-3 term as used herein encompasses synthetic peptides comprising one or more 14-3-3 recognition motifs.

The term 14-3-3 recognition motif or 14-3-3 recognition site or 14-3-3 binding site as used herein refers to an amino acid sequence comprising the sequence RSXpSXP where X is any amino acid and the "pS" designation is a phosphorylated serine residue.

The term 14-3-3 binding protein as used herein refers to a 14-3-3 protein capable of binding to a 14-3-3 binding site.

The term TcAK1 substrate as used herein refers to a natural or synthetic peptide or protein comprising an amino acid sequence recognized by TcAK1 as a site for phosphorylation.

The term phosphatase as used herein refers to a general term for an enzyme that catalyzes hydrolysis of a phosphate ester. Many highly specific protein phosphatases are known to function as regulators of activity, acting in concert with kinases to fine tune the activity of cellular processes.

The term DNA Sequence as used herein denotes a sequence of polydeoxynucleotides containing genetic information. Both cDNA (obtained by copying messenger RNA) and genomic DNA are included in the term "DNA sequence." Many DNA sequences are originally cloned as cDNA. Once a cDNA clone is available, genomic DNA can be obtained without undue experimentation, by techniques known in the art. For most eukaryotic genes, genomic DNA includes sequences not found in cDNA. These include introns, regulatory regions, polyadenylation signals and the like. By convention, DNA sequences are written in the direction from the 5' end to the 3' end of that strand whose sequence is that of the corresponding messenger RNA, sometimes called the "sense" strand.

The term expression as used herein is used to denote processes by which the information content of a DNA sequence is converted to an observable function. Typically, the term refers to transcription (MRNA synthesis) and/or translation (encoded protein synthesis) of coding regions. However, non-coding regions can also be expressed, usually resulting in a regulatory effect. When a cloned DNA sequence is expressed in a heterologous cell, the expression can either be direct (where only sequences contained within the cloned DNA sequence are translated) or through synthesis of a fusion protein (including translation of an additional coding sequence). A sequence is "expressible" when combined in appropriate orientation and position with respect to control sequences (promoter, ribosome binding site, polyadenylation site, etc.) that are operative in the desired host cell as is well-known in the art.

The term coding as used herein refers generally to the relationship between the nucleotide sequence of a DNA segment, and the amino acid sequence to which it corresponds, according to the known relationship of the genetic code. As is well known, a sequence of three nucleotides (triplet) encodes a single amino acid. Each of the twenty principal amino acids is encoded by at least one triplet, and most are encoded by more than one. Consequently, a single amino acid sequence can be encoded by a large number of different triplets. All the DNA sequences that encode the same amino acid sequence (synonymous codings) are therefore equivalent, although certain individual sequences may prove advantageous in certain types of host cells. Once a single coding sequence has been cloned, a person of ordinary skill in the art can readily make equivalent synonymous sequences by known methods, without undue experimentation. As used herein, a DNA sequence is said to encode a given amino acid sequence if it includes a nucleotide sequence that is translatable to the corresponding amino acid sequence. The coding nucleotide sequence may also include one or more introns, as well as untranslated nucleotide sequences, and sequences encoding other amino acid sequences.

The term chimeric as used herein is a term describing a non-naturally occurring combination of two or more different DNA sequences expressible as a single amino acid sequence, a chimeric protein. The source of the different sequences can be from the same or different species or from synthetic, non- naturally occurring sequences. A chimeric protein can have separate functions attributable to the different sequences, or the different sequences can contribute to a single function. [An example of the former is given herein for synthesis of CDNA encoding a myc epitope at the N-terminus of TcAK1. The expressed chimeric myc-TcAK1 protein combines the functions of TcAK1 with ability to bind to an anti-myc antibody.] An example of a chimeric protein where the different parts contribute a single function would be a Xenopus-human hybrid TcAK1 or other interspecies hybrid, or even a combination of a non-naturally-occurring sequence substituted for a portion of TcAK1. Typical chimeric amino acid sequences of the invention will include the TcAK1 sequence combined with an added sequence that provides an additional function, e.g., where the added amino acid sequence is an epitope, has catalytic activity, is a cellular localization signal or confers a specific binding property. It will be understood that the foregoing functions need not be mutually exclusive. A specific binding property can, for example, be the specific binding of a substrate associated with catalytic (enzyme) activity or it could be the property of binding an antibody or it could simply be the ability to bind to an affinity chromatography ligand. A cellular localization signal can result in concentration of the chimeric amino acid sequence in the cell nucleus, on the endoplasmic reticulum, into an organelle or in transport to the cell exterior. Amino acid sequences conferring such properties are known in the art.

The term heteroloqous as used herein is a term applied to an in vivo expression system where the host cells are of a different species than the DNA sequence expressed. An example herein is given by the expression of TcAK1 in cultured insect cells. Typically, use of a heterologous expression system requires combining the coding sequence with a control sequence known to function in the heterologous host cell (a heterologous control sequence). Where TcAK1 is expressed in insect cells, a baculovirus promoter (from an insect-pathogenic virus) is provided as the control region.

The term control sequence as used herein is the term used for an untranslated DNA sequence that can function to insure expression, affect rate of expression, lifetime of mRNA and the like. Examples of control sequences include promoters, operators, enhancers, ribosome binding sites, polyadenylation signals and the like, as known in the art.

The term non-human sequence as used herein is used to denote a sequence known to have a source from a species other than human, including a synthetic source.

The term antibody as used herein is used herein to include both monoclonal and polyclonal antibodies as well as antibody fragments. An antibody is "specifically reactive" with a protein or epitope if it binds with the protein or epitope preferentially compared to other proteins or epitopes which may be present in the same mixture. An antibody can be "cross-reactive" with another (usually similar) protein or epitope. However, under equilibrium conditions, antibody will be more strongly bound to a protein or epitope to which it is specifically reactive than to one to which it is merely cross-reactive.

The term an internal C-terminal peptide as used herein refers to a stretch of amino acids comprised in the amino acid sequence of a TcAK1 kinase, e.g., a stretch of approximately thirteen or greater amino acids located at the C-terminus of the TcAK1 protein or a stretch of approximately thirteen amino acids located internally.

The term TcAK1 as used herein refers to a protein kinase which catalyzes the phosphorylation of the Ser 216 of Cdc25C. The phosphorylation exerts a regulatory effect on Cdc25C activity, permitting the latter to associate with a 14-3-3 protein. Association of Cdc25C with a 14-3-3 protein provides a linkage between cell cycle regulation and external or internal cell signals which increase or decrease the cell replication rate.

The term hybridize under stringent conditions as used herein refers to hybridization carried out under optimal reaction conditions of temperature, ionic strength and time of reaction which permit selective hybridization between oligomers and eliminate nondiscriminate hybridization. In a preferred embodiment of the invention, hybridization was carried out at a temperature of 42° C. for 16–20 hours in 2×PIPES buffer (0.8M NaCl, 20 mM PIPES buffer, pH 6.5), 50% of formamide, 0.5% SDS, 100 mg/ml denatured salmon sperm DNA, followed by a sequence of fifteen-minute washes at 42° C.–55° C. in 2×or less SSC medium with 0.1% SDS.

The term a level of interaction significantly different from that obtained for the corresponding . . . as used herein refers to the condition wherein the level of protein interaction using a mutated protein is detectably greater than or less than the level of protein interaction using a corresponding non-mutated protein.

TcAK1 protein was purified 8000-fold from rat liver and enzyme activity was identified with a 36–38 kD doublet by SDS-polyacrylamide gel electrophoresis [Ogg et al., (1994) supra]. An amino terminal amino acid segment of the p36 was determined and the sequence is presented in FIG. 1A (SEQ ID NO:3). A database scan yielded a sequence match for a protein denoted "p78." Although a sequence of p78 was present in GenBank (Accession M80359), no information was presented other than it was a 78 kD marker protein lost in chemically induced transplantable carcinoma and primary carcinoma of human pancreas. Despite the lack of characterization and the great difference of molecular weights, PCR primers were constructed from the 5' and 3' terminal sequences of p78 and used to obtain a full-length cDNA from a human B-cell library. The sequence of the PCR product revealed (see FIG. 1B) several differences from the p78 sequence: seven single nucleotide differences resulting in seven amino acid substitutions and an additional 48 nucleotides encoding 16 amino acids inserted between residues 370 and 371 of p78. The seven amino acid differences were Q125E; K139E; G409A; T440S; D500A; T587N and K605E. (The number is the position in the sequence, the preceding letter is the p78-encoded amino acid, the letter following is the TcAK1-encoded amino acid). The PCR product was used to probe a HeLa cell cDNA library from which several cDNAs were obtained and sequenced. A full length cDNA (#6) was found to have the nucleotide sequence (SEQ ID NO:1), presented in FIG. 1B, which was shown to encode TcAK1 protein. The sequence of the cDNA#6 (SEQ ID NO:1) was identical to that of the PCR product except for the substitution of glycine for serine at position 443 and a silent substitution of A for C at the third position of the threonine 438 codon.

The predicted open reading frame of TcAK1(SEQ ID NO:1) encodes a protein of 729 amino acids (SEQ ID NO:2). The kinase domain is found in the N-terminal portion of the molecule encompassing amino acids 54–310 (FIG. 1B).

TcAK1 was expressed in several human cancer cell lines as revealed (see FIG. 2A) by the presence of mRNAs of approximately 3.8 and 3.1 in all lines tested. Northern analysis performed using mRNAs derived from a variety of human tissues (brain, placenta, lung, liver, skeletal muscle, kidney and pancreas) revealed the same size transcripts. An additional mRNA of ~3.0 was observed in heart tissue.

TcAK1 expression in a cell or tissue can be detected and/or quantified with a TcAK1 DNA probe comprising a DNA sequence encoding a TcAK1 kinase or a characteristic portion thereof, e.g., the kinase domain, etc., to form a nucleic acid hybrid under stringent conditions between the TcAK1 DNA and any corresponding nucleic acid present in the cell or tissue. After separating the nucleic acid hybrid with art known methods, e.g., electrophoresis, etc., the amount of TcAK1 DNA present in the nucleic acid hybrid can be quantitated and related to total TcAK1 expression in the cell or tissue.

Figure 2B:
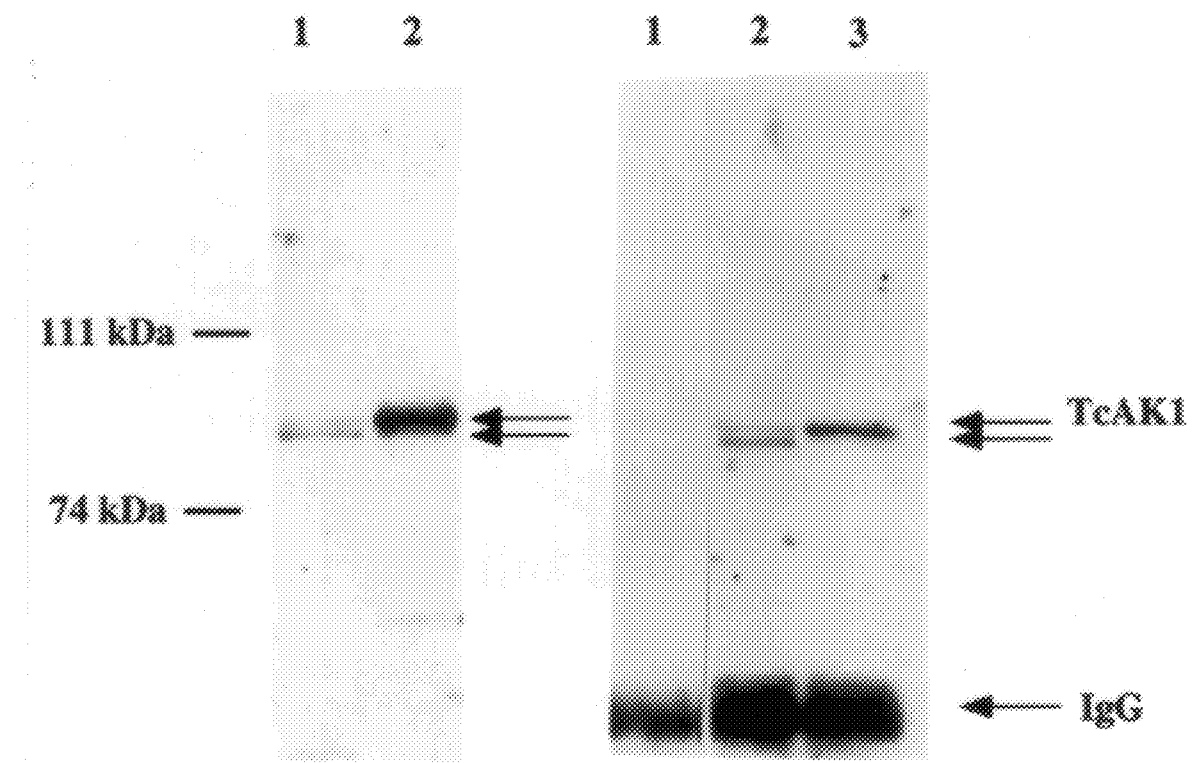
Figure 2C:
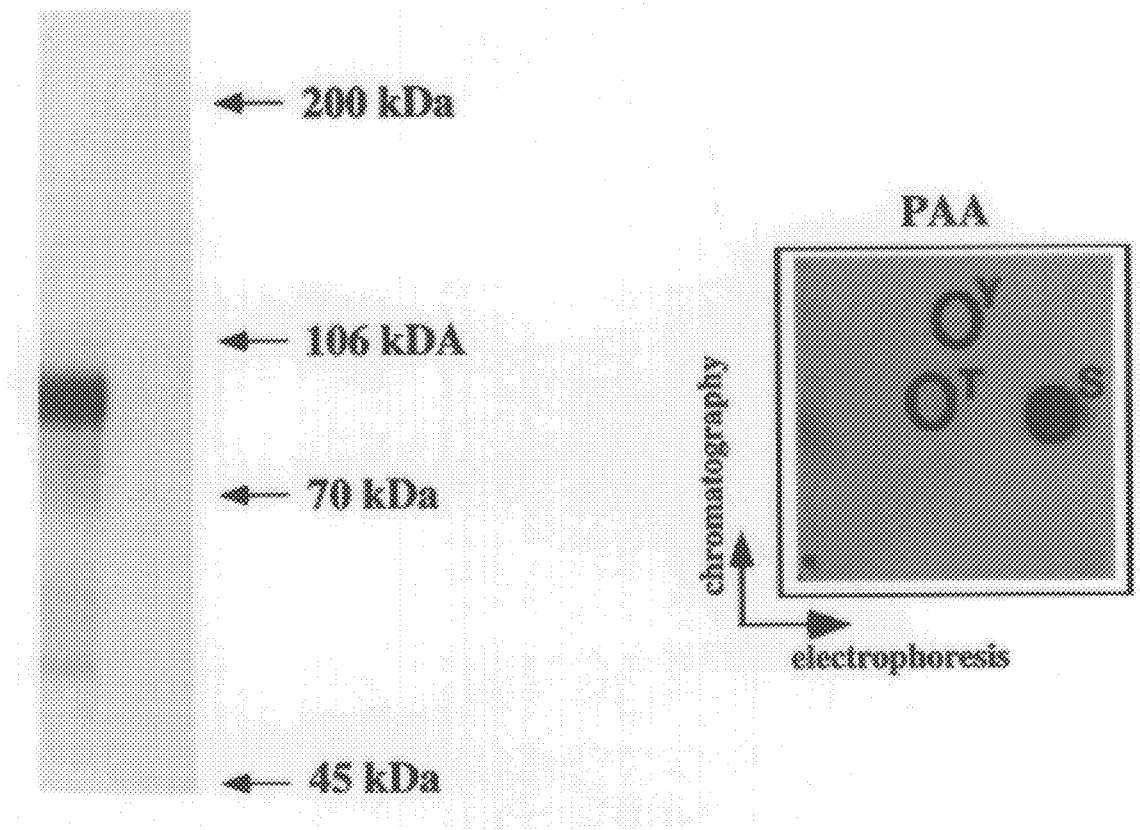

TcAK1 protein expression in HeLa and Jurkat cells was detected with affinity purified TcAK1-specific antibodies (FIG. 2B). In HeLa cells, TcAK1 resolved as a doublet of approximately 78 and 80 kDa whereas in Jurkat cells the 80 kDa form predominated. Also, recombinant TcAK1 was expressed as a histidine tagged-fusion protein in bacteria and was found to be catalytically active with autophosphorylation occurring on serine residues as illustrated in FIG. 2C.

Figure 3A:
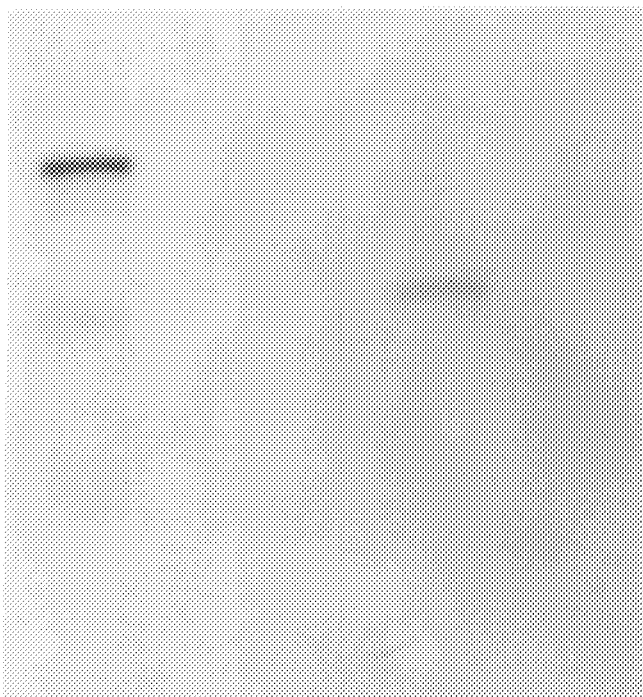
Figure 3C:
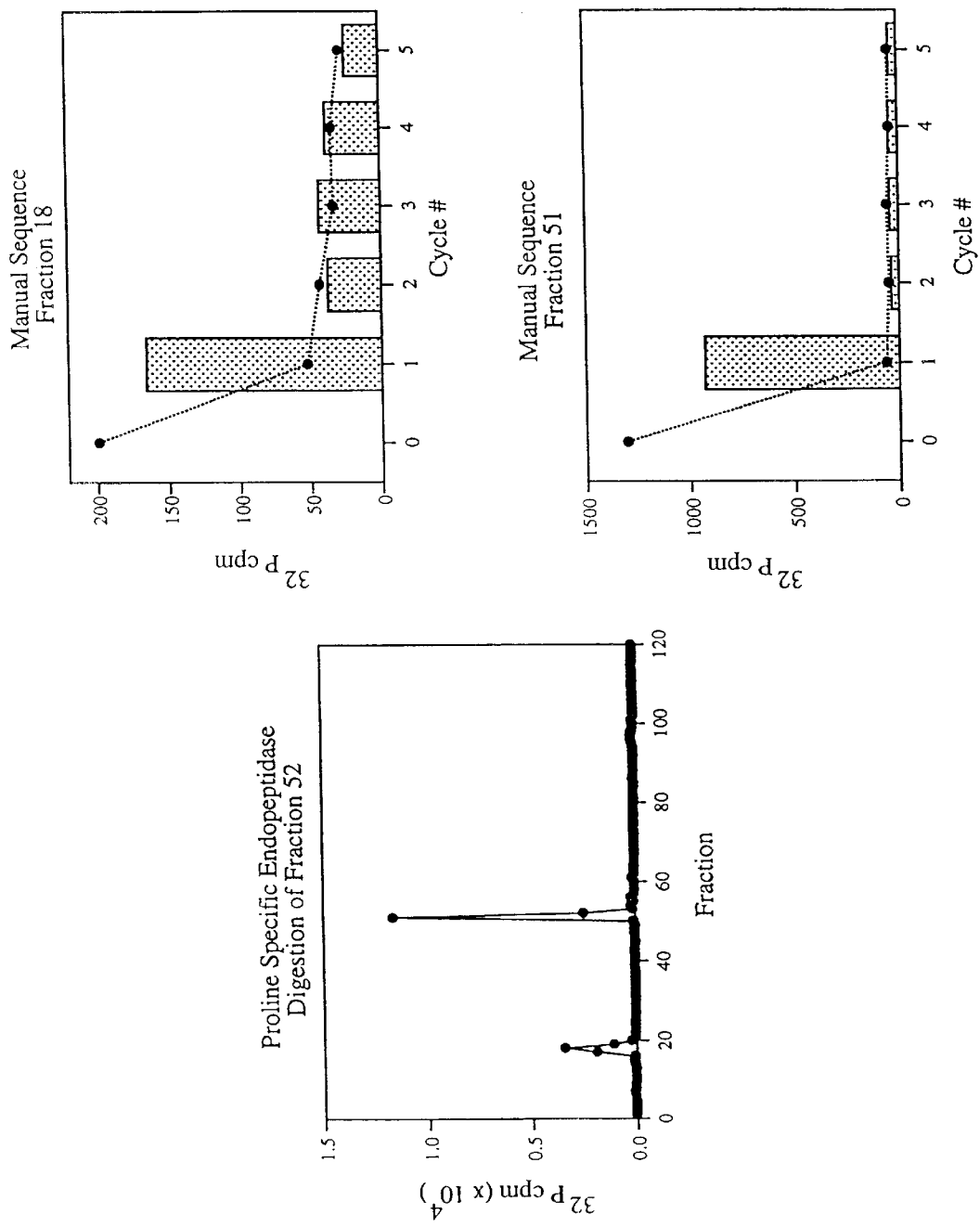

TcAK1 was originally purified based on its ability to bind to Cdc25C (within a domain bordered by amino acids 200 to 256) and to phosphorylate Cdc25C on serine 216 (Ogg et al., 1994). Recombinant TcAK1 was determined to be capable of phosphorylating Cdc25C on serine 216. As shown in FIG. 3A, bacterial TcAK1 phosphorylated full length Cdc25C (FIG. 3A, lane 1) as well as a deletion mutant containing the N-terminal 258 amino acids of Cdc25C [(N258), lane 3]. Substitution of alanine for serine at position 216 ablated the phosphorylation of N258 and greatly reduced the phosphorylation of Cdc25C by TcAK1 (FIG. 3A, lanes 2, 4). Manual Edman degradation identified serine 216 as the major site of TcAK1 phosphorylation (FIGS. 3B and 3C). A minor site of phosphorylation was observed within the C-terminus of Cdc25C.

Substrate specificity of TcAK1 was evaluated with a series of peptides synthesized to reflect a region of Cdc25C surrounding serine 216. These peptides were synthesized to correspond to amino acids 210–231 of human Cdc25C (Ogg et al. 1994, supra) containing serines at positions 214 and 216 (SPS) or containing substitutions of serine 214 with alanine (APS) or serine 216 with either alanine (SPA) or threonine (SPT). Substrate specificity was evaluated for the HeLa cell Cdc25C-associated kinase capable of binding to GST-Cdc25C in vitro (GST, glutathione S-transferase; Ogg et al., 1994). Bacterially produced GST and GST-motif were purified on GSH beads and immobilized proteins were incubated with HeLa cell extracts, washed, and assayed for kinase activity in the presence of each of the peptides. As shown in FIG. 4, the Cdc25C-associated kinase preferentially phosphorylated peptides containing serine 216 (upper panel). Peptides containing either alanine or threonine in place of serine at position 216 were not efficiently phosphorylated in vitro. Substitution of serine 214 with alanine had no apparent effect on peptide phosphorylation. Substrate specificity of endogenous TcAK1 was also determined. Immunoprecipitates of TcAK1 from HeLa cells showed the same selectivity for a serine at position 216 (lower panel) as did bacterially produced TcAK1. Also evaluated was whether a kinase having the same specificity as TcAK1 could be detected in Cdc25C immunoprecipitates. As shown in FIG. 4, immunoprecipitates of Cdc25C contained a protein kinase with the same selectivity for serine at position 216 (lower panel).

The binding specificity of recombinant TcAK1 is presented in FIG. 5. Cdc25C and various deletion mutants were expressed in bacteria as GST-fusion proteins and subsequently purified on GSH agarose (FIG. 5, left panel). Each protein was tested for its ability to bind to TcAK1 that had been overproduced in insect cells. As shown in FIG. 5 (right panel) neither GST (lane 1) nor the C-terminus of Cdc25C (lane 4) bound to TcAK1. However, both full length Cdc25C (lane 2) and the N-terminal 258 amino acids of Cdc25 bound to TcAK1 (lane 3). Also, the Cdc25C motif region (bordered by amino acids 200 to 256) bound to recombinant TcAK1 (lane 5).

The Cdc25C motif was also able to bind to endogenous HeLa and Jurkat cell TcAK1. GST and GST-motif proteins were expressed in bacteria and bound to GSH agarose. Recombinant proteins were incubated with lysates prepared from either HeLa or Jurkat cells. Bound proteins were incubated with lysates prepared from either HeLa or Jurkat cells. Bound proteins were resolved by SDS-PAGE and the presence of TcAK1 was monitored by immunoblotting. As shown in FIG. 6, the Cdc25C motif bound to endogenous TcAK1 present in both HeLa (left panel, lane 4) and Jurkat cells (right panel, lane 4).

Figure 7A:
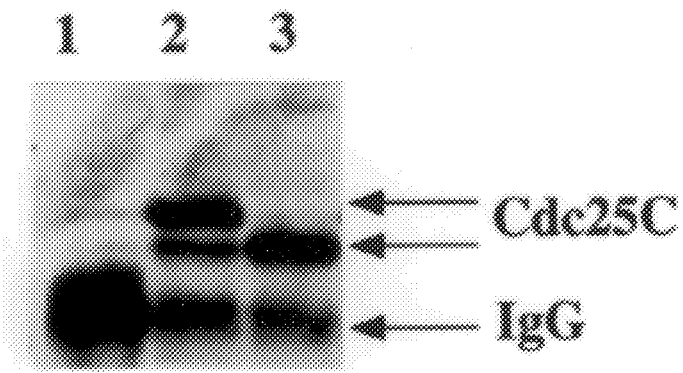
Figure 7B:
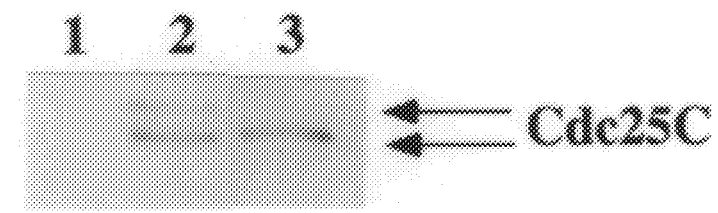

Serine 216 phosphorylation and TcAK1 activity were determined throughout the cell cycle. As shown previously the predominant site of Cdc25C phosphorylation in asynchronously growing HeLa cells is serine 216. Phosphorylation of Cdc25C on serine 216 retards the electrophoretic mobility of Cdc25C in SDS gels (see FIG. 7). This property can be used to monitor and/or quantitate the levels of serine 216-phosphorylated Cdc25C in vivo. As shown in FIG. 7A, the majority of Cdc25C is retarded in its electrophoretic mobility (lane 2) indicative of serine 216 phosphorylation. When cell lysis and immunoprecipitation reactions were carried out in the absence of microcystin, the faster electrophoretic form of Cdc25C predominated (FIG. 7A, lane 3). Transient transfection of HeLa cells with plasmids encoding Myc-epitope tagged Cdc25C resulted in approximately 40% of the Cdc25C being converted to the slower electrophoretic form indicative of serine 216 phosphorylation (FIG. 7B, lane 2), indicating that the serine 216 kinase is active under these conditions. Substitution of serine 216 with alanine prevented the phosphorylation of Cdc25C on serine 216 and, therefore, only the faster electrophoretic form of Cdc25C was detected (FIG. 7B, lane 3).

Figure 8A:
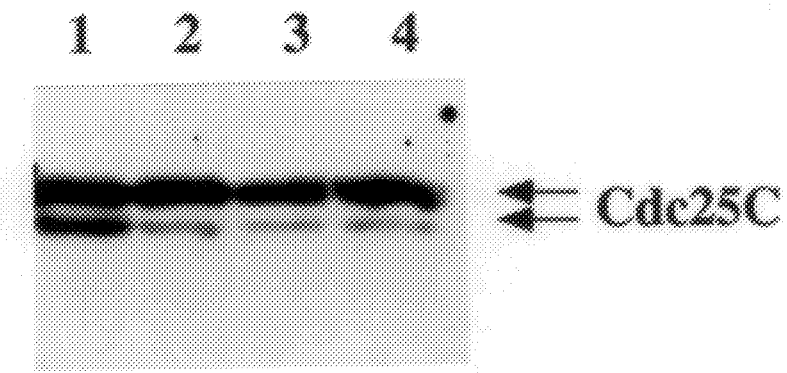
Figure 8B:
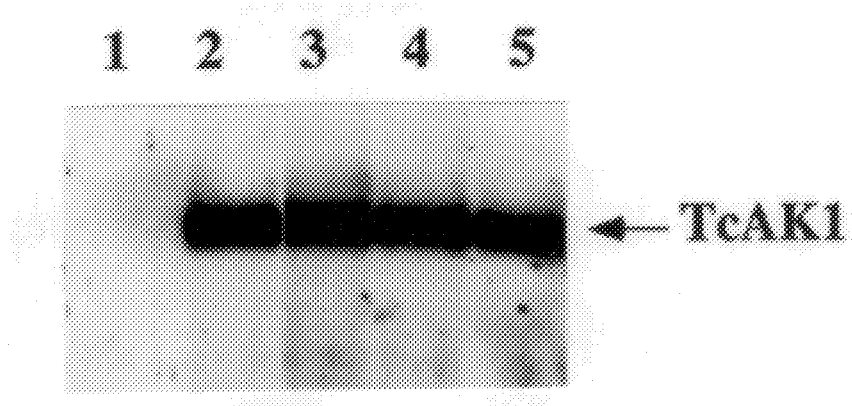
Figure 8C:
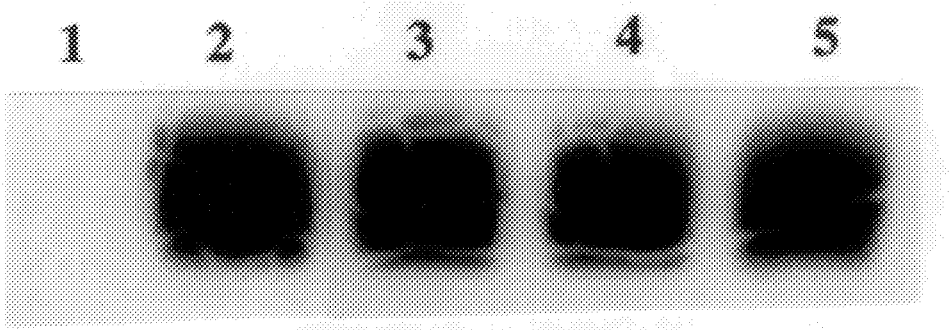

To determine whether phosphorylation of Cdc25C on serine 216 was cell cycle regulated, Jurkat cells were elutriated and fractions were analyzed for Cdc25C by immunoblotting. As seen in FIG. 8A (top panel), the majority of Cdc25C was phosphorylated on serine 216 throughout the G1-(lane 2);S-(lane 3) and G2-phases of the cell cycle (lane 4), indicating that serine 216 phosphorylation was constitutive throughout most of the cell cycle. During mitosis, Cdc25C undergoes major shifts in its electrophoretic mobility due to N-terminal phosphorylations (Izumi et al., 1992; Kumagai and Dunphy, 1992; Hoffmann et al., 1993; Villa-Moruzzi, 1993) and, thus, it was not possible to determine the state of serine 216 phosphorylation in mitosis by immunoblotting. If, however, TcAK1 is the serine 216 kinase, it might be predicted that the activity of TcAK1 would also be constitutive throughout the G1-, S- and G2-phases of the cell cycle. Indeed, as shown with immunoblotting experiments (FIG. 8B, middle panel) the levels of TcAK1 remained constant throughout these phases of the cell cycle. In addition, immune complex kinase assays performed in the presence of the APS peptide (corresponds to amino acids 210–231 of human Cdc25C with a substitution of alanine for serine at position 214) demonstrated that TcAK1 activity was also constant (FIG. 8C, lower panels).

Cdc25C was shown to interact directly with 14-3-3 protein and this interaction was shown to be dependent upon Cdc25C being phosphorylated on serine 216. The "recognition motif" for 14-3-3 binding consists of the sequence RSXpSXP where X is any amino acid and the underlined serine is phosphorylated [Muslin et al, (1996) Cell 84: 889–897). This consensus motif fits perfectly the sequence bordering and inclusive of serine 216 in Cdc25C (RSPS$_{216}$MP). Various forms of Cdc25C were tested for binding to 14-3-3 in insect cells. FIG. 9 illustrates the interaction between 14-3-3 and Cdc25C (lane 3) as well as the N-terminal 258 amino acids of Cdc25C(N258, lane 2) was detected. The C-terminus of Cdc25C (lane 1) was negative in this assay. Furthermore, 14-3-3 binding was independent of phosphatase activity, since a catalytically inactive form of Cdc25C also bound to 14-3-3 (lane 4), localizing the 14-3-3 interaction to the N-terminus of Cdc25C.

Figure 10A:
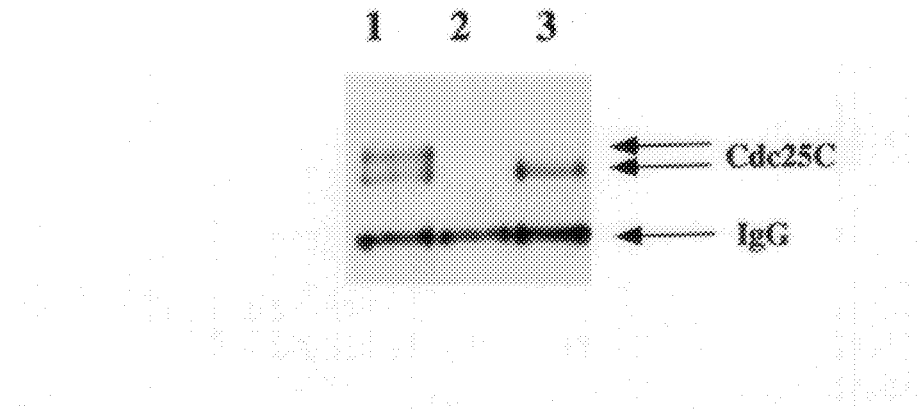
Figure 10B:
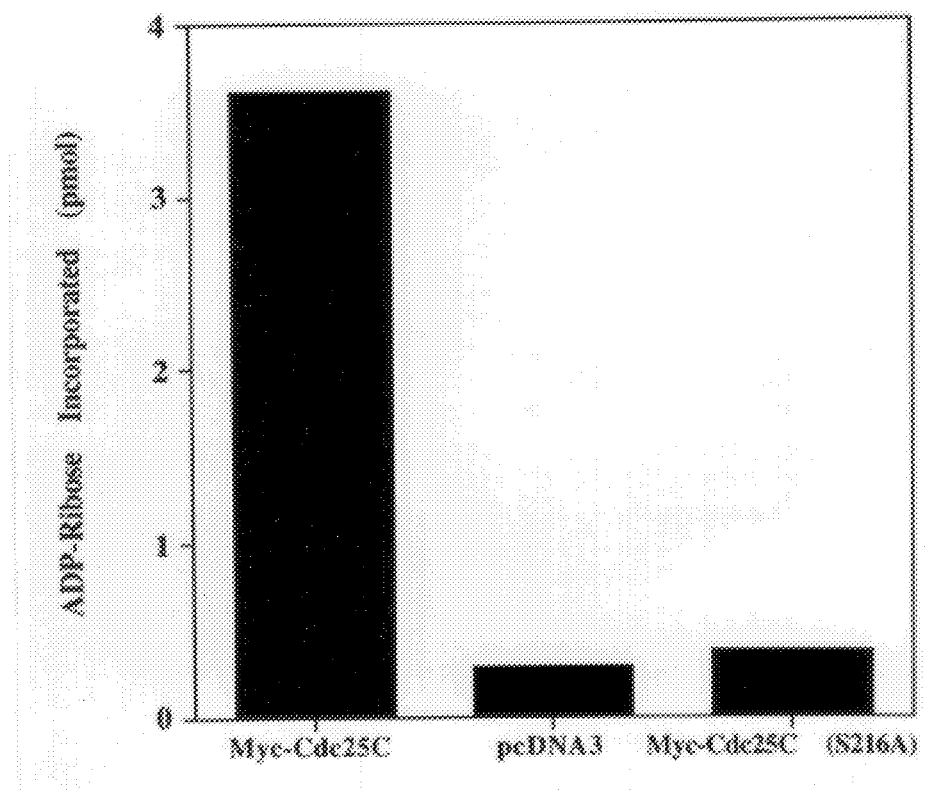

The association between Cdc25C and 14-3-3 was also examined in HeLa cells by transiently expressing Cdc25C and the serine 216 mutant of Cdc25C as myc-epitope tagged proteins. At 31 hours after transfection, Cdc25C and Cdc25CS216A were immunoprecipitated with monoclonal antibodies to the myc-epitope tag. One half of each immunoprecipitate was assayed for Cdc25C my immunoblotting (FIG. 10A), the second half was assayed for the presence of 14-3-3 using an enzymatic assay that measures exoenzyme S activity (FIG. 10B). Because 14-3-3 migrates in the same region of the gel as the light chain of IgG, its presence is difficult to detect using standard one dimensional SDS-PAGE and immunoblotting. Therefore, an enzymatic assay based on the fact that 14-3-3 serves as cofactor in vitro for an adenosine 5'-diphosphate (ADP)-ribosyltransferase enzyme (exoenzyme S) from *Pseudomonas aeruginisa* was used. As shown in FIG. 10A, Cdc25C resolved as a doublet in SDS gels (lane 1) whereas Cdc25CS216A migrated as a single electrophoretic form (lane 3). Cdc25C was not detected in control immunoprecipitates (lane 2). The slower electrophoretic form of Cdc25C represents serine 216 phosphorylated Cdc25C. As shown in FIG. 10B, Cdc25C immunoprecipitates activated ADP-ribosylation by exoenzyme S. Immunoprecipitates from control cells or cells overproducing Cdc25S216 were significantly lower in this assay. These results indicate a specific interaction between Cdc25C and 14-3-3 and illustrate the importance of serine 216 in this interaction.

Figure 11A:
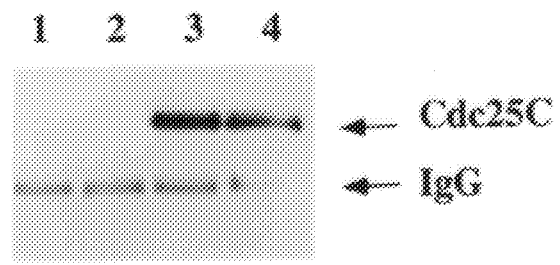
Figure 11B:
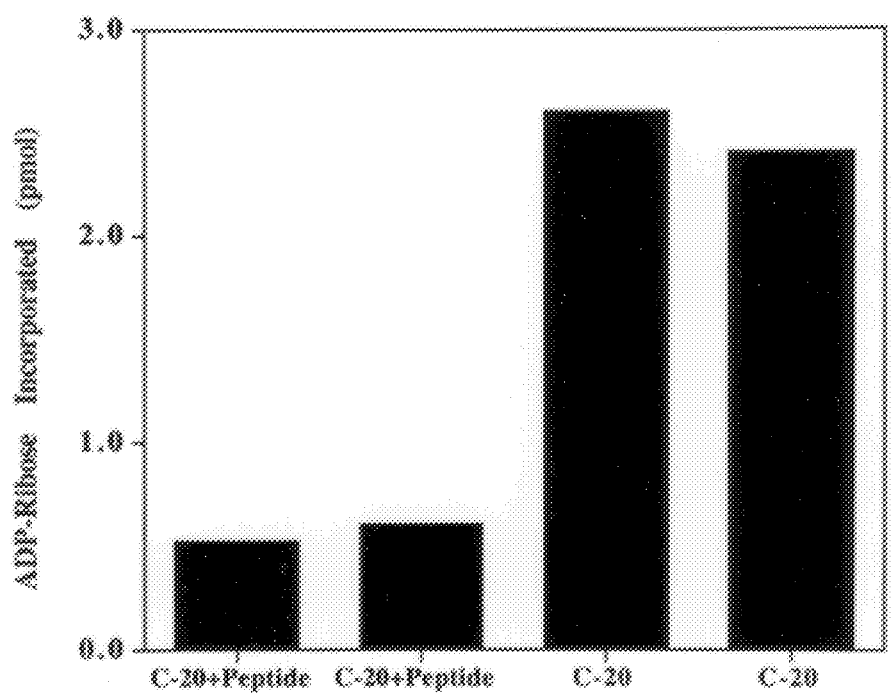

To assay for an interaction between 14-3-3 and endogenous Cdc25C, immunoprecipitates were prepared from HeLa cell lysates using an antibody against the carboxy-terminal peptide of human Cdc25C (FIG. 11). Half of the immunoprecipitate was immunoblotted for the presence of Cdc25C (FIG. 11A) and half was assayed for activation of exoenzyme S activity (FIG. 11B). As shown in FIG. 11, exoenzyme S activity specifically immunoprecipitated with Cdc25C. Cdc25C was not detectably precipitated when the antibody was pre-incubated with the immunogenic peptide (FIG. 11A, lanes 1, 2) nor were there significant levels of exoenzyme S activity in the precipitate (FIG. 11B). These results indicate a functional interaction between Cdc25C and 14-3-3 in vivo.

The interaction between Cdc25C and 14-3-3 was shown by phosphorylation of serine 216. Insect cells were infected with recombinant baculoviruses encoding Cdc25C. When produced in insect cells, the majority of Cdc256C was not phosphorylated and migrated in SDS gels as the faster electrophoretic form (FIG. 12, lane 1). However, a minor population of Cdc25C was phosphorylated on serine 216 and migrated as the slower electrophoretic form (FIG. 12, lane 2). A binding assay was performed in vitro to determine which form of Cdc25C preferentially interacted with 14-3-3. Recombinant 14-3-3 fused to GST was purified from bacteria and was incubated with lysates prepared from Cdc25C-overproducing insect cells. Bound proteins were washed, resolved by SDS-PAGE and Cdc25C was detected by immunoblotting. As seen in FIG. 12 (lane 2), only the serine 216-phosphorylated form of Cdc25C (slower electrophoretic form) bound to GST-14-3-3 in this assay, demonstrating the importance of phosphorylated serine 216 for this interaction.

TcAK1 functions not only to mediate the interaction between 14-3-3 and Cdc25C, but also plays a more general role in mediating the interaction between 14-3-3 and other cellular proteins that have been shown to either mediate oncogenesis or key signalling events. Various 14-3-3 isoforms have been found in complexes with oncogenes (the middle T antigen of polyoma virus and Bcr-Abl), and signaling molecules (c-Raf1, c-Bcr and PI3K). Mutations in these proteins and in proteins present in pathways involving these proteins are associated with human cancers. Participation of TcAK1 in these pathways was shown by the demonstration that TcAK1 phosphorylates RAF1 on serine 259 and 621 in vitro (the two sites that regulate RAF1/14-3-3 binding in vivo).

Mutations in 14-3-3 proteins or TcAK1 substrates that prevent or interfere with the TcAK1 phosphorylation-specific interaction between a 14-3-3 protein and a TcAK1 substrate are detected by the methods of this invention. Such mutations are recognized and/or determined by measuring the extent of TcAK1 phosphorylation-specific interaction between a mutated 14-3-3 protein and a TcAK1 substrate or a mutated TcAK1 substrate and a 14-3-3 protein in a cell or tissue transformed with a DNA sequence encoding a TcAK1 protein and comparing it to the extent of interaction obtained with the corresponding non-mutated protein.

It will be apparent to those of ordinary skill in the art that alternative methods, reagents, procedures and techniques other than those specifically detailed herein can be employed or readily adapted to practice the detection methods of this invention. Such alternative methods, reagents, procedures and techniques are within the spirit and scope of this invention.

The methods of this invention are further illustrated in the following non-limiting Examples. All abbreviations used herein are standard abbreviations in the art. Specific procedures not described in detail in the Examples are well-known in the art.

EXAMPLE 1

Purification and Sequencing of Rat Liver Cdc25C-Associated Kinase (Rat TcAK1)

To obtain protein sequence information, 202 g of rat liver was used to purify TcAK1. Purification of the kinase was performed essentially as described in Ogg et al., 1994 supra. Briefly, the homogenate was divided into two parts and each half was individually fractionated over a S-Sepharose Fast Flow column (Pharmacia). Fractions from each separation that contained peak Cdc25C associated kinase activity were pooled and the purification was continued through a buffer exchange column, a Q-Sepharose column (Pharmacia), an ATP-agarose column (Sigma), another buffer exchange column, a Resource S column (Pharmacia) and finally a Superose-12 10/30 column (Pharmacia). Fractions from the Superose-12 10/30 that contained the peak of the activity were concentrated using Centricon-10 concentrators (Amicon). Proteins were resolved on an 11% SDS-polyacrylamide gel and visualized by staining with 1% Coomassie brilliant blue (w/v). The protein band corresponding to TcAK1 was excised from the gel and placed in the well of a 10%-T, 3% C gel with a 4% T, 3% C stacking gel as described (Schagger and von Jagow, 1987). The gel slice was overlaid with 200 µl of sample buffer containing 0.1 µg Staphylococcal V-8 protease. Samples were electrophoresed until the proteins were stacked up at the stacking/resolving gel interface and then the electrophoresis was stopped. After a 1 h incubation, the electrophoresis was continued to completion. The gel was then transferred to PolyScreen PVDF Transfer Membrane (NEN Research Products). Proteins were visualized by staining for 1 min in 0.1% Coomassie blue/50% methanol (w/v) and destaining in 10% acetic acid/40% methanol (v/v/v). Protein sequence was obtained by automated Edman degradation and analysis, using an Applied Biosystems 477 protein sequencer and Applied Biosystems 120.

EXAMPLE 2

Constructs of Cdc25C and Mutants Thereof

A: Construction of pUC19-Cdc25C. A 1.4 Ban HI-Pfl MI fragment encoding Cdc25C was excised from pML25 (Lee et al., (1992) treated with Klenow and ligated to phosphorylated Xba I Lingers. The fragment was inserted into the polylinker of pUC19 to generate pUC19-Cdc25C.

B. Construction of pGC52-N258 and pGC52-N258 (S216A). Site directed mutagenesis of the codon for serine 216 of Cdc25C was performed using an oligonucleotide directed mutagenesis kit (Amersham). A 774 pb Bam HI-Eco RI fragment encoding the N-terminal 258 amino acids of Cdc25C was excised from pGEX2T-N258 (Lee et al., 1992) and inserted into the polylinker of pGC52 (obtained by Bam HI-Eco RI digestion of pSAF10 (Parker et al., 1991) to excise the 1.2 kb cdc2 fragment) to generate pGC52-N258. Single-stranded pGC52-N258 was mutagenized using the oligo 5' ATATCGCTCCCCG GCGATGCCAGAGAACTT3' (SEQ ID NO:5), where underlined codon, residue 216, encoded Ala rather than Ser, generating pGC52-N258(S216A).

C. Construction of pGEX2T-N258(S216A). The 774 bp Bam HI-Eco RI fragment encoding N258(S216A) was excised from pGC52-N258(S216A) and inserted into the polylinker of pGEX2T to generate pGEX2T-N258(S216A).

D. Construction of pUC19-Cdc25C(S216A). A 330 pb Bal I fragment encoding the S216A mutation was excised from pGC52-N258(S216A) and inserted into the corresponding Bal I site in pUC19-Cdc25C to generate pUC19-Cdc25C(S216A).

E. Construction of pGEX2T-Cdc25C(S216A). A 1.2 kb Ppu MI-Nsi I fragment encoding the S216A mutation was excised from pUC19-Cdc25c(S216A) and inserted into the corresponding sites of pML25 to generate pGEX2T-Cdc25C (S216A).

F. Construction of pFASTBAC1-Cdc25C(S216A) and generation of recombinant baculovirus. A 1.9 kb Bam HI fragment encoding Cdc25C(S216A) was excised from pGEX2T-Cdc25C(S216A) and inserted into the polylinker of pFASTBAC1, generating pFASTBAC1-Cdc25C (S216A). Recombinant baculovirus encoding Cdc25S216A was generated according to the manufacturer's recommendations (Gibco BRL).

G. N-terminal myc-epitope Cdc25C fusion constructs. The first 300 nucleotidase of Cdc25C were amplified by PCR using wild type Cdc25C as template with a 5' primer coding for the myc epitope EQKLISEEDL (SEQ ID NO:17) and containing a Hind III site, and a 3' primer containing a Bst EII site [5' primer, CAGCATAAGCTTACCATGGCA-GAACAGAAGCTCATTTCTGAAGAAGACTTGTCT ACGGAACTCTTCTCA (SEQ ID NO:6); 3' primer, AAT-GCACTTCCTGAAGTCCTGAAGA (SEQ ID NO:7)]. The conditions for the PCR were as follows: 20 ng of template, 0.3 mM each deoxynucleoside triphosphate, 1 µM each primer, 4 mM $MgSO_4$, and 2 U of Vent DNA polymerase (New England Biolabs, Beverly, Mass.); thermal cycles: 1 at 94° C. for 10 min; 3 at 94° C. for 90 s, 45° C. for 30 s, 50° C. for 30 s, 72° C. for 20 s; and 32 at 94° C. for 90 s, 60° C. for 60 s, 72° C. for 20 s. The amplified DNA was digested with Bst EII and Hind III, followed by purification of the 350 pb fragment by agarose gel electrophoresis and Qiaquick Gel Extraction (Qiagen, Chatsworth, Calif.). The resulting fragment was ligated into the purified 6.5 kb Bst EII/Hind III backbone-fragment of both pRc/CMV-Cdc25C wild type and S216A mutant, followed by transformation of E. coli JM109. Plasmids were then isolated from single bacterial clones and checked both by restriction digest and sequencing.

H. Construction of pET15b-Cdc25C. A 2.0 kb Bam HI fragment encoding Cdc25C was excised from pML25 (Lee et al., 1992), blunt ended with DNA polymerase I large (Klenow) fragment and ligated to Nde I digested and Klenow-treated pET15b (Novagen).

I. Construction of pFASTBAC1-His$_6$Cdc25C. pET15b-Cdc25C was digested with Nco I and Bam HI, Klenow-treated and the 2 kb His$_6$Cdc25C fragment was subcloned into pFASTBAC1 (Gibco BRL) that had been digested with Bam HI and Klenow-treated. Recombinant baculovirus encoding His$_6$-Cdc25C was generated according to the manufacturer's recommendations (Gibco BRL).

J. Construction of pET-15b(mod)Cdc25C(S216A). The pET-15b vector was modified by addition of a 10-mer oligonucleotide 5'-TCGAGGTACC-3'(SEQ ID NO:8) into the Xho I site of the polylinker to generate pET-15b(mod). This creates a Kpn I site and changes the reading frame of the Bam HI site in the polylinker. A 1.9 kb Bam HI fragment encoding Cdc25c(S216A) was excised from pGEX-2T and inserted into the polylinker of pET-15b(mod).

K. Construction of pFASTBAC1-His$_6$Cdc25C(S216A). A 1.9 kb Xba I-Sma I fragment encoding His$_6$Cdc25C(S216A) was excised from pET-15b(mod), the Xba I overhang was filled in with DNA polymerase I large (Klenow) fragment, and inserted into the Stu I site of pFASTBAC1.

L. Construction of a catalytically inactive form of Cdc25C(C377S). To create a phosphatase-dead version of Cdc25C, serine was substituted for cysteine at position 377. The full-length Cdc25C cDNA was excised as an Xba I fragment from pUC19-Cdc25C and subcloned into the Xba I site of pGC52. The resulting plasmid was then digested with Sma I and Dra I and the 3.5 kb backbone containing the C-terminal 215 amino acids of Cdc25C was isolated, religated and used to transform the CJ236 bacterial strain. Single-stranded DNA was prepared from the bacterial culture superinfected with helper phage M13K07. Next, the oligonucleotide CGTGTTCCA CTCTGAATTCTCCTCAGAGAGGGGCCC CCGGATGTGCCGC (SEQ ID NO:9) (encoding serine for cysteine at position 377 and containing a silent mutation which creates a Hpa II site for screening of mutants) was annealed to the single stranded DNA and the complementary strand was synthesized. The reaction mixture was used to transform MV1190 to recover the double stranded DNA. Mutants were screened by performing a Hpa II digest of the miniprep DNA. The detailed procedures of the mutagenesis was essentially as described in the instruction manual of Muta-gene phagemid in vitro mutagenesis kit (BIO-RAD). The Bgl II to Nsi I fragment of pUC19-Cdc25C was replaced with the corresponding fragment containing the C377S mutation to generate the full length Cdc25C(C377S) mutant. The Ppu MI to Nsi I fragment of Cdc25C in the pGEX2TCdc25C was in turn replaced with the corresponding fragment from the pUC19 Cdc25C(C377S) to generate pGEX2TCdc25C(C377S) construct.

M. Construction of pFASTBAC1-Cdc25C(C377S). A 1.9 kb Bam HI fragment encoding Cdc25C(S216A) was excised from PGEX-2T and inserted into the polylinker of pFAST-BAC1.

N. Construction of pGEX2TB-Cdc25C(C377S). A 1.9 kb Bam HI fragment encoding Cdc25C(C377S) was excised from pGEX-2T and inserted into the polylinker of pGEX-2TB.

O. Construction of pFASTBAC1-GST-Cdc25C(C377S). pGEX2TB-Cdc25C(C377S) was digested with Xba I and Sma I and the fragment containing GST-Cdc25C(C377S) was subcloned into the Stu I site of pFASTBAC1. Recombinant baculoviruses were generated as described below.

EXAMPLE 3

Constructs of TcAK1 and Mutants Thereof

3A. Creation of pGEX-2TN(TcAK1) and pGEX-2TN [TcAK1(1-412)]. TcAK1 proteins: Human TcAK1 and TcAK1(1–412) were obtained by polymerase chain reaction (PCR) amplification from a B lymphocyte cDNA library [gift of S. J. Elledge, (Durfee et al., 1993)] using the oligonucleotides: 5'-CGAGT CATATGTCCACTAGGACCCC-3' (SEQ ID NO:10) and either 5'-CCAGT CATATGTTAACTTACAGCTTTAGCTCATTTGGC-3' (SEQ ID NO:11) for TcAK1 or 5'-CCAGT CATATGTTAACTTAGCTTGAAGAAACA CTTCTCTGC-3'(SEQ ID NO:12) for TcAK1(1–412). To obtain enough TcAK1 DNA for subcloning it was necessary to reamplify the initial PCR product. The regions of the primers that are underlined are Nde I restriction sites which were used to ligate the PCR products into linearized pGEX-2TN (gift of Dr. Giulio Draetta) to generate pGEX-2TN (TcAK1) and pGEX-2TN(TcAK1(1–412)].

Creation of a kinase-deficient form of TcAK1. To create a catalytically-inactive form of TcAK1, alanine was substituted for asparagine at position 183 using a PCR based site-directed mutagenesis strategy. To achieve this, the following two mutagenic primers: 5'-CAAGGCTGAA GCTCTATTGTTAGATGC-3'(SEQ ID NO:13) and 5'-GCATCTAACAATAGAGCTTCAGCCTTG-3' (SEQ ID NO:14) were used in conjunction with the two TcAK1 primers described above to amplify a 1187 pb product in which the codon AAT was changed to GCT (underlined). The PCR product was digested with Bgl II and Xba I, and 427 bp fragment was isolated and used to replace the same region of wild-type TcAK1 in pGEX-2TN (to generate pGEX-2TN[TcAK1(N183A)]. The mutation was confirmed by sequencing.

3B. Construction of pET.TcAK1 and pET.TcAK1 (N183A). Wild-type and kinase-deficient TcAK1 were engineered for expression in *Escherichia coli* with $NH_2$-terminal hexahistidine tags. To achieve this, pGEX-2TN(TcAK1) and pGEX-2TN[TcAK1(N183A)] were digested with NdeI and ligated to the pET15b vector (Novagen) which had been previously linearized with Nde I. The resulting plasmids are referred to as pET.TcAK1 or pET.TcAK1(N183A) for wild-type TcAK1 and kinase-deficient TcAK1, respectively.

EXAMPLE 4

Library Screening for TCAK1 cDNAs

To obtain a full-length human TcAK1 cDNA, a lambda ZAP II HeLa cDNA library was screened according to the manufacturer's instructions (Stragene). A total of $1 \times 10^6$ phage were plated and then lifted onto nylon membrane filters (NEN). The DNA was denatured and filters were UV-irradiated to crosslink the DNA. To make the probe, the Nde I-Xba I fragment of TcAK1(1–899) was isolated from pGEX 2TN p78 and labeled with dCTP($\alpha$-$^{32}$P) using the Megaprime DNA Labeling System (Amersham). The filters were prehybridized with 2X PIPES buffer (0.8M NaCl,20 mM PIPES buffer, pH 6.5), 50% formamide, 0.5% SDS, 100 mg/ml denatured salmon sperm DNA at 42° C. for 6 hours, then hybridized with the labeled probe in the same buffer at 42° C. for 16–20 hours. The filters were washed with 2×SSC, 0.1% SDS at room temperature for 15 mins, with 0.1×SSC, 0.1% SDS twice at 42° C. for 15 mins each time, three times at 50° C. for 15 min, and three times at 55° C. for 15 min. They were then subjected to autoradiography at −80° C. overnight. Positive clones were picked, plated and subjected to two additional rounds of plaque purification. pBluescript phagemids containing the cDNA inserts were excised in vivo from the parental lambda ZAP II vector. The cDNA sequences were determined by direct automated DNA sequencing.

Northern Analysis. pGEX-2TN[TcAK1(1–412)] was digested with Nde I and the 1.1 kb fragment encoding the kinase domain of TcAK1 was labeled with ($^{32}$P) $\alpha$-dCTP using the Megaprime DNA Labeling System (Amersham). A human cancer cell line MTN blot (Clontech) was probed and processed according to the manufacturer's instructions.

EXAMPLE 5

Expression and Purification of TcAK1 and Mutants Thereof

5A. Expression and purification of Hexahistidine-tagged TcAK1. The *E. coli* strain BL21(DE3) was transformed with either the pET.TcAK1 or pET.TcAK1(N183A). Cultures were grown at 37° C. until reaching an $A_{600}$ of ~0.6 at which time the T7RNA polymerase was induced with 100 $\mu$M isopropyl-1-thio-$\beta$-D-galactopyranoside (IPTG). After induction, cells were grown at 28° C. for 11 h, collected by centrifugation at 5000×g for 10 min, and resuspended in IMAC-5 buffer (20 mM Tris (pH 7.5), 500 mM NaCl and 50 mM imidazole) supplemented with 2 mM phenylmethylsulfonyl fluoride, 10 $\mu$g/ml aprotinin, 20 $\mu$M leupeptin, and 5 $\mu$g/ml pepstatin. Cells were lysed by one treatment with a French press at 1000 p.s.i. and lysates were clarified by centrifugation at 50,000×g for 30 min. The supernatant was batch-absorbed to $Ni^{2+}$-NTA-agarose (Qiagen) for 1 h at 4° C. and the resin collected by centrifugation at 5000×g for 10 min. Following washing with 5 column volumes of IMAC-5 buffer, the resin was washed with 2 column volumes of IMAC-50 buffer [20 mM Tris (pH 7.5), 500 mM NaCl and 50 mM imidazole] and TcAK1 was eluted with IMAC-100 (20 mM Tris (pH 7.5), 500 mM NaCl and 100 mM imidazole).

5B. Autophosphorylation of TCAK1. Wild-type TcAK1 or TcAK1(N183A) was incubated for 1 h at 30° C. in buffer D (75 mM Tris-HCl, pH 7.5, 10mM $MgCl_2$, and 1 mM DTT) supplemented with 200 μM ATP and 30 μCi of $\gamma$-$^{32}$P ATP. Reactions were terminated by the addition of 3×SDS-sample buffer followed by heating at 100° C. for 10 min. Samples were resolved by electrophoresis on an 8% SDS gel and visualized by staining with Coomassie Blue and autoradiography.

5C. Detection of TcAK1 in HeLa and Jurkat cells. HeLa and Jurkat cells (~1×10$^7$) were washed twice in PBS and then lysed in 1 ml of mammalian cell lysis buffer consisting of 50 mM Tris pH 8.0, 2 mM DTT, 5 mM EDTA (pH 8.0), 0.1% NP-40, 100 mM NaCl, 1 mM microcystin, 50 mM NaF, 1 mM sodium orthovanadate, 2 mM PMSF, 0.15 U/ml aprotinin, 20 mM leupeptin, and 20 mM pepstatin for 30 min. at 4° C. Lysates were clarified and 2 mg of protein were incubated with 5 μl of affinity-purified TcAK1 antibody at 4° C. for 2 h followed by incubation for an additional 1 h at 4° C. in the presence of 30 μl of a 50% slurry of Sepharose CL-4B protein A beads. Beads were washed four times in lysis buffer, boiled in protein sample buffer for 10 min., and then resolved on an 8% SDS-gel. Alternatively clarified lysates containing 200 μg of total cellular protein were boiled directly in sample buffer and resolved on an 8% SDS gel. Proteins were transferred to nitrocellulose membranes. Membranes were incubated in blocking buffer (5% milk in 10 mM Tris (pH 8.0), 150 mM NaCl, and 0.3% Tween 20) at room temperature for 1 h; followed by incubation with affinity-purified TcAK1 antibody (at 1:10,000 dilution) in washing buffer (10 mM Tris, pH 8.0, 150 mM NaCl, and 0.3% Tween 20) at room temperature for 1 h. Membranes were subjected to four 15 min. washes in wash buffer and then processed to visualize TcAK1. HRP-conjugated protein A (Amersham) was used as secondary antibody (at a 1:5000 dilution).

5D. HPLC analysis and manual sequencing. Proteins were separated by SDS-PAGE, transferred to nitrocellulose and visualized by autoradiography. The nitrocellulose containing radiolabeled GST-Cdc25C was excised, blocked with 0.5% polyvinylpyrrolidone (PVP-40) in 100 mM acetic acid for 30 min. at 37° C., washed three times with water and digested with TPCK trypsin (Worthington) at a final concentration of 0.03 μg/ml in 0.1M $NH_4CO_3$(pH8.0) for 2 h at 37° C. Two additional 2 h incubations were carried out at 37° C. in the presence of fresh trypsin (15 μg each). Further digestion on selected HPLC fractions was performed with 2 units of proline specific endopeptidase (ICN) in 0.1M sodium phosphate, 5 mM EDTA (pH 7.4) at 37° C. for 16 hr.

Reactions were acidified in 1% trifluoroacetic acid (TFA) and loaded onto a Vydac C18 column (25 cm×0.46 cm I.D.). Reverse phase HPLC was performed at 37° C. Reactions were loaded in 0.1% TFA (Buffer A) and eluted with a gradient from 0 to 60% Buffer B (90 acetonitrile, 0.95% TFA). Fractions were collected at 0.5 min intervals and counted for radioactivity. Selected fractions were immobilized on Sequenlon-AA membrane discs (Millipore) for amino-terminal sequencing. Manual Edman degradation was performed as described (Bodwell et al., 1991; Sullivan and Wong, 1991) with a coupling and cleavage temperature of 55° C.

EXAMPLE 6

Antibodies

6A. Preparation of Antibodies. Antibodies to TcAK1 were prepared using bacterial GST-TcAK1 as antigen or using peptide antigens composed of either the C-terminal 13 amino acids of TcAK1 (KNIASKIANELKL) (SEQ ID NO:15) or a stretch of 13 amino acids (KQKDENKEAKPRS) (SEQ ID NO:16) located internally. Both peptides contained a cysteine residue at their N-termini and were coupled to keyhole limpet hemocyanin (KLH). Two antibodies were used for the detection of Cdc25C: an affinity purified polyclonal antibody (see below) and a polyclonal antibody directed against a C-terminal peptide of Cdc25C (C-20, Santa Cruz Biotechnology). In all cases, bound primary antibodies were detected using horseradish-peroxidase conjugated anti-rabbit or anti-mouse secondary antibodies (Cappel) and an ECL detection system (Amersham).

6B. Preparation of affinity columns. Two liters of induced bacterial culture expressing hexahistidine ($His_6$)-tagged TcAK1 were pelleted and resuspended in 180 ml of homogenization buffer consisting of 50 mM Tris (pH 7.5), 500 mM NaCl supplemented with protease inhibitors (2 mM PMSF, 0.15 U/ml aprotinin, 20 mM leupeptin, and 20 mM pepstatin). Cells were lysed with one pass through a French Press at 1000 psi. Clarified lysates were incubated with 4 ml prepared Ni-NTA agarose beads (Qiagen) at 4° C. for 1 h. Beads were washed with IMAC 50 buffer and eluted with IMAC 100 buffer. Eluted TcAK1 was first concentrated by dialysis against a solution consisting of 20% polyethylene glycol (MW 15,000 to 20,000) in 50 mM Tris (pH 7.5), 200 mM NaCl, followed by dialyzed against 0.1M $NaHCO_3$, 0.5M NaCl (pH 8.3) at 4° C. overnight. TcAK1 was covalently coupled to 1.5 gram of activated CH Sepharose 4B at room temperature for 3 h. Blocking and washings were performed according to the manufacturer's instructions. Preparation of the affinity column for Cdc25C antibodies was performed as described previously (Ogg et al., 1994).

6C. Affinity purification of TcAK1 and Cdc25C(N258) antibodies. CST-TcAK1 antisera was passed over the His-TcAK1 affinity column at 4° C. overnight. The column was washed with RIPA buffer (20 mM Tris pH 7.4, 137 mM NaCl, 10% glycerol, 0.1% SDS, 0.5% sodium deoxycholate, 1% Triton X-100, 2 mM EDTA) followed by NETN buffer (20 mM Tris pH 8, 1 mM EDTA, 0.5% NP-40) containing 0.5M NaCl. Antibodies specific for TcAK1 were eluted first with 100 mM glycine (pH 2.5) and then with 0.1M triethylamine. All fractions containing antibodies were neutralized with 1M Tris (pH 8.0), pooled and adjusted to 0.1 mg/ml Bovine serum albumin. Proteins were precipitated with 50% ammonium sulfate (w/v) and centrifugation. Pellets were resuspended in and dialyzed against Tris buffered saline (10 mM Tris pH 8.0, 0.5M NaCl). Antibodies were aliquoted and stored at −80° C. The purification of anti-N258 Cdc25C antibodies was essentially the same except that polyclonal GST-25C antisera was first passed over a GST-Sepharose column to remove antibodies specific for GST. Unbound antisera was loaded onto a GST-25(N258)-Sepharose column.

EXAMPLE 7

Interaction of Cdc2SC with TcAK1

7A. Phosphorylation of Cdc25C by TcAK1 in vitro: Induction and purification of GST-fusion proteins: JM109 cells were transformed with plasmids encoding GST-Cdc25C, GST-CdcC(S216A), GST-N258, and GST-N258 (S216A). 20 mL of overnight culture was used to inoculate 2 L of Luria Broth (containing 100 ug/mL ampicillin). The culture was grown at 37° C. to an O.D.$_{600}$ of 0.6. IPTG was added to a final concentration of 0.5 mM and the culture was incubated for 3 hours at 30° C. The cells were collected by centrifugation at 3800×g for 10 min.

Bacterial pellets were washed with PBS and then resuspended in 120 mL of STE (100 mM NaCl, 10 mM Tris HCl, 1 mM EDTA, pH 8.0) supplemented with 2 mM PMSF, 0.15 U/mL aprotinin, 20 μM leupeptin, 20 μM pepstatin, and 0.5 mg/mL lysozyme, and rocked at 4° C. for 20 min. 21.2 mL of 10% sarkosyl (N-lauroylsarcosine, Sigma, L-5125) in STE was added (1.5% final concentration) and lysed by sonication. Lysates were clarified by centrifugation at 15,000×g for 10 min., and 35 mL 10% Triton X-100 (Sigma, X-100) in STE was added (2% final concentration). 20 mL packed glutathione (GSH) agarose beads (Sigma, G-4510) was incubated with the clarified lysates for two hours at 4° C. Pelleted beads were washed twice in STE, twice in LiCl Buffer (0.5M LiCl, 50 mM Tris HCl, pH 8.0), and twice in 50 mM Tris HCl, pH 7.4. Washed beads were packed into two 10 mL reusable columns (Econo-Column Chromatography Columns, Biorad), and GST-fusion proteins were eluted with 20 mM glutathione (Sigma, G-4251) in 50 mM Tris pH 7.4. 0.5 mL fractions were collected and peak fractions were pooled, dialyzed overnight in 25 mM Tris-HCl, pH 7.4, and frozen at −80° C. The concentration of each GST-fusion construct was estimated by comparison to known BSA standards after SDS-PAGE and Coomassie blue staining.

Kinase assays: Kinase reactions consisted of 1 μg of purified His-tagged TcAK1, 5 μg of GST-fusion protein (GST-Cdc25C, GST-Cdc25C(S216A), GST-N258, or GST-N258(S216A) in 40 μL of complete kinase buffer (50 mM Tris pH 7.4, 10mM MgCl$_2$, 2 mM DTT, 10 μM ATP, and 10 uCiγ-$^{32}$P ATP (>4000 Ci/mmol). Reactions were incubated at 30° C. for 20 minutes, and then boiled in SDS-sample buffer, resolved by SDS-PAGE (7% gel), proteins were visualized by Coomassie blue staining and by autoradiography.

7B. Peptide kinase assays. Preparation of HeLa cell lysates: HeLa cells (~1×10$^7$) were washed twice in PBS and then lysed in 1 ml of mammalian cell lysis buffer consisting of 50 mM Tris pH 8.0, 2 mM DTT, 5 mM EDTA pH 8.0, 0.1% NP-40, 100 mM NaCl, 1 mM microcystin, 50 mM NaF, 1 mM sodium orthovanadate, 2 mM PMSF, 0.15 U/ml aprotinin, 20 mM leupeptin, and 20 mM pepstatin for 30 min. at 4° C. Lysates were clarified and incubated with either GST-fusion proteins (as outlined below) or with affinity purified antibodies. Lysates containing ~750 μg of protein were incubated with 5 μl of either N258 antibody or TcAK1 antibody at 4° C. for 1 h followed by an additional 1 h at 4° C. in the presence of 30 μl of a 50% slurry of sepharose CL-4B protein A beads. Beads were pelleted and washed four times with lysis buffer and twice with incomplete kinase buffer (50 mM Tris pH 7.5, 10 mM MgCl$_2$, and 2 mM DTT).

Preparation of recombinant GST-fusion protein: Bacteria expressing GST or GST-Cdc25C(motif) were suspended in STE (100 mM NaCl, 10 mM Tris HCl, 1 mM EDTA, pH 8.0) supplemented with 2 mM PMSF, 0.15 U/mL aprotinin, 20 μM leupeptin, 20 μM pepstatin, and 1.0 mg/mL lysozyme, and rocked at 4° C. for 20 min. The solution was adjusted to 1.5% sarkosyl (N-lauroylsarcosine, Sigma, L-5125) and bacteria were lysed by sonication. The lysate was clarified by centrifugation at 3200×g for 20 min and Triton X-100 (Sigma) was added to a final concentration for 2%. Approximately 1 μg of GST-fusion protein was bound to 15 μl packed glutathione (GSH) agarose beads (Sigma) for 45 min at 4° C. Pelleted beads were washed twice with NETN buffer containing 1M NaCl, followed by twice with NETN buffer and then incubated with HeLa cell lysate (1.5 mg) at 4° C. for 1 h. Beads were pelleted and washed four times with mammalian cell lysis buffer and twice with incomplete kinase buffer twice (50 mM Tris (pH 7.5), 10 mM MgCl$_2$, and 2 mM DTT).

Kinase reactions: 40 μl kinase reactions containing approximately 1 μg of GST-fusion protein bound to 15 μl of GSH agarose beads, 5 μM peptide, 50 mM Tris (pH 7.5), 10mM MgCl$_{21}$ 2 mM DTT, 20 μM ATP, 10 uCi γ-$^{32}$P ATP (>4000 Ci/mmol), were incubated at 30° C. for 10 minutes. Immune complex kinase assays were incubated at 30° C. for 20 min. Reactions were resolved on a 20% SDS polyacrylamide gel, dried and subjected to autoradiography.

7C. Binding specificity of Cdc25C and TcAK1.

Preparation of insect cell lysate: Sf9 cells were infected with recombinant baculovirus encoding TcAK1. Atd 40 h post infection, cells (~2×10$^7$) were rinsed twice in PBS and then lysed in 2 ml of NETN buffer (20 mM Tris pH 8.0, 1 mM EDTA, 100 mM NaCl, 0.5% NP-40) supplemented with 1 mM DTT, 1 mM Na$_3$VO$_4$, 10 mM NaF, 1 μM microcystin, 0.15 unit/ml aprotinin, 20 μM leupeptin, 20 μM pepstatin, and 2 mM PMSF.

Preparation of GST-proteins and binding assay: Induced bacterial pellets expressing GST, GST-Cdc25C, GST-Cdc25C(N258), GST-25C(C215) and GST-25C motif were suspended in STE supplemented with 2 mM PMSF, 0.15 U/mL aprotinin, 20 μM leupeptin, 20 μM pepstatin, and 1.0 mg/mL lysozyme, and rocked at 4° C. for 20 min. The solution was adjusted to 1.5% sarkosyl (N-Lauroyl Sarcosine, Sigma, L-5125) and bacteria were lysed by sonication. The lysate was clarified by centrifugation at 3200×g for 20 min and Triton X-100 (Sigma) was added to a final concentration of 2%. 4 μg of each protein were bound to 50 μl of packed GSH agarose beads by incubation at 4° C. for 45 min. Beads were washed 3 times with NETN. Half of the beads were resolved directly on a 10% SDS gel and proteins were visualized by staining the gel with Coomassie blue. The second half was incubated with insect cell lysate (~400 ug). Bound proteins were washed 4 times with NETN, resolved on a 7% SDS gel and transferred to nitrocellulose. Membranes were incubated with antibodies raised against an internal TcAK1 peptide (KQKDENKEAKPRS) at a 1:1,000 dilution.

7D. Binding of Cdc25C-motif to endogenous TCAK1 in vitro.

Preparation of cell lysate: HeLa and Jurkat cells (~6×10$^7$) were rinsed twice in PBS and then lysed in 6 ml of NETN Buffer (20 mM Tris pH 8.0, 1 mM EDTA, 100 mM NaCl, 0.5% NP-40) supplemented with 1 mM DTT, 1 mM Na$_3$VO$_4$, 10 mM NaF, 1 μM microcystin, 0.15 unit/ml aprotinin, 20 μM leupeptin, 20 μM pepstatin, and 2 mM PMSF.

Preparation of GST-proteins and binding assay: Induced bacterial pellets expressing GST and GST-25C(motif) were lysed by sonication in STE (25 mM Tris pH 8.0, 150 mM NaCl, 1 mM EDTA) supplemented with 1.5% sarcosyl. 4 μg of each protein were bound to 50 μl of packed GSH agarose beads by incubation at 4° C. for 45 minutes. Beads were washed 3 times with NETN (20 mM Tris pH 8.0, 1 mM EDTA, 100 mM NaCl, 0.5% NP-40). Half of the beads were resolved directly on a 7% SDS gel, the other half was incubated with either HeLa (~2 mg) or Jurkat (~1 mg) lysates at 4° C. for 1 h. Bound proteins were washed 4 times with NETN, resolved on a 7% SDS gel and transferred to nitrocellulose. Membranes were incubated with affinity purified TcAK1 antibody at 1:10,000 dilution.

EXAMPLE 8

Interaction of Cdc25c With 14-3-3 Protein

8A. Association of Cdc25C with 14-3-3 in insect cells. Sf9 cells were infected with viruses encoding GST-Cdc25C, GST-N258, GST-Cdc25C(C377S), and GST-C215. In other experiments, cells were infected with viruses encoding hexahistidine tagged forms of Cdc25C or Cdc25C(S216A) in the absence of presence of viruses encoding 14-3-3 (zeta isoform). For GST-fusion proteins, cells were lysed in buffer A. For hexahistidine tagged proteins, cells were lysed in buffer B. Lysates were clarified by centrifugation at 13,000×g for 15 min. To ~1.5 mg of protein was added 50 $\mu$L of a 50% suspension of GSH agarose (Sigma) or 50 $\mu$L $Ni^{2+}$-NTA-agarose (Qiagen) for cells expressing GST-fusion or hexahistidine tagged forms of Cdc25C, respectively. Following incubation for 30 min at 4° C., GSH agarose or $Ni^{2+}$-NTA-agarose was collected by centrifugation in a microfuge at maximum speed for 10 sec. Beads were washed 3 times with 1 ml buffer A (GSH-agarose) or buffer B ($Ni^{2+}$-NTA-agarose). $Ni^{2+}$-NTA-agarose beads were washed once more with buffer B containing 50 mM imidazole. SDS sample buffer was added and samples were heated for 10 min at 100° C. Samples were subjected to 12.5% SDS-PAGE and transferred to nitrocellulose membrane. Nitrocellulose membranes were cut in half and the top portion immunoblotted for either GST using a GST rabbit polyclonal antibody or for Cdc25C using the E10 antibody. The lower half was blotted for 14-3-3 using 14-3-3 β (K-19, Santa Cruz).

8B. Expression of Cdc25C and Cdc25C (S216A) in HeLa cells and Immunoprecipitations from HeLa and Jurkat cells. Approximately $3 \times 10^5$ HeLa cells were seeded per 35 cm tissue culture dish and allowed to grow for 24 hrs in DMEM (high glucose; Gibco-BRL) containing 10% fetal calf serum. Cells were transfected with vectors encoding myc-Cdc25C or myc-Cdc25C (S216A) in $pcDNA_3$ (Invitrogen) using lipfectamine (Gibco-BRL) according to the manufacturer's instructions. Cells were also transfected with the empty vector ($pcDNA_3$) as a control. At 31 hrs post transfection, cells were washed twice in ice-cold PBS, and then lysed in buffer A. Cells were then snap-frozen and stored in liquid nitrogen until future use. Frozen lysates were thawed and then rocked on a nutator for 10 min at 4° C. Lysates were clarified by centrifugation at 13,000×g for 15 min and pre-cleared by incubation with Sepharose CL-4B protein A beads (Sigma). Jurkat cell lysates (prepared from untransfected Jurkat cells grown to sub-confluency) were prepared in a similar manner. For immunoprecipitations of endogenous Cdc25C from Jurkat cells, either the E10 monoclonal antibody or the C-20 antibody (Santa Cruz) were used. To ~3.5 mg of protein was added either 155 $\mu$L of the E10 supernatant or 155 $\mu$L of supernatant containing monoclonal antibody specific for GST (as a control). As a control for the C-20 immunoprecipitations, the C20 antibody was pre-incubated with a synthetic peptide consisting of the C-terminal 20 amino acids of Cdc25C for 20 min at 4° C. Immunoprecipitations were performed for 2 hrs at 4° C. followed by the addition of 50 $\mu$L of a 50% solution of Sepharose CL-4B protein A beads (Sigma) for an additional 30 min. For immunoprecipitations of myc-epitope tagged proteins, 20 $\mu$L of myc-agarose (Santa Cruz) was added to ~1 mg of transfected HeLa cell lysate and allowed to incubate at 4° C. for 3 hrs. The Sepharose CL-4B protein A beads or the myc-agarose was isolated by centrifugation in a microfuge at maximum speed for 1 sec, and washed four times with 1 ml of buffer A. One half of the sample was resolved directly by SDS-PAGE and processed for immunoblotting, the other half assayed for the presence of 14-3-3 as described below.

8C. ADP-ribosylation assays. ADP-ribosylation assays were performed as described previously (Coburn et al., 1991; Fu et al., 1993). Immunoprecipitates from either Jurkat or HeLa cells were incubated with reaction mixtures containing 5 $\mu$M (adenylate-$^{32}$P)NAD(NEN), 100 $\mu$g/ml soybean trypsin inhibitor (Sigma), and Exoenzyme S (UBI) at 1 $\mu$g/ml in a total volume of 20 $\mu$L. Reactions were carried out for 20 min at 25° C. and then terminated by either spotting 10 $\mu$L onto p-81 paper, or mixing with SDS sample buffer. P81 papers were washed in 0.75% phosphoric acid three times and once with acetone prior to scintillation counting. Specific incorporation of ($^{32}$P)NAD into soybean trypsin inhibitor was confirmed by analysis of the reaction on 12.5% SDS-PAGE. Radiolabeled species were excised and $^{32}$P-incorporation quantitated by scintillation counting.

EXAMPLE 9

Buffers

Buffer A consisted of: phosphate-buffered saline (PBS: 137 mM NaCl, 2.7 mM KCl, 4.3 mM $Na_2HPO4$, 1.5 mM $KH_2PO_4$, pH 7.4) supplemented with 1% NP-40, 5 mM EDTA, 1 mM sodium vanadate, 1 $\mu$M microcystin-LR (Gibco-BRL), 2 mM dithiothreitol (DTT), 10 $\mu$g/ml aprotinin, 20 $\mu$M leupeptin, and 5 $\mu$g/ml pepstatin. Buffer B is identical to buffer A except it lacks EDTA and DTT. Buffer C consisted of 20 mM Tris (pH 7.5), 500 mM NaCl, 5 mM imidazole, 2 mM phenylmethylsulfonyl fluoride (PMSF), 10 $\mu$g/ml aprotinin, 20 $\mu$M leupeptin, and 5 $\mu$g/ml pepstatin. Buffer D consisted of: 75 mM Tris-HCl, pH 7.5, 10 mM $MgCl_2$, and 1 mM DTT.

---

I claim:

1. A DNA sequence encoding the amino acid sequence of TcAK1, as set forth in SEQ ID NO:2.

2. A DNA sequence according to claim 1 wherein said DNA sequence is that set forth in SEQ ID NO:1.

3. A transformed cell comprising a DNA sequence according to claim 1 combined with a heterologous control sequence and expressible in said cell.

4. A transformed cell according to claim 3 wherein said cell is a non-human cell.

5. A transformed cell comprising said DNA sequence according to claim 2 combined with a heterologous control sequence and expressible in said cell.

6. A transformed cell according to claim 5 wherein said cell is a non-human cell.

7. A method for detecting and quantifying TcAK1 expression in a cell or tissue sample comprising:

hybridizing mRNA obtained from the sample with an excess of labeled TcAK1 DNA encoding the amino acid of TcAK1 as set forth in SEQ ID NO:2, or the kinase domain thereof, thereby forming an RNA:DNA hybrid under stringent conditions between the labeled TcAK1 DNA and any TcAK1 mRNA present in the cell or tissue sample;

separating the RNA:DNA hybrid from any unhybridized TcAK1 DNA; and detecting and/or quantifying the amount of TcAK1 DNA present in an RNA:DNA hybrid, whereby TcAK1 expression in the sample is detected and quantified.

8. A method of claim 7 wherein the separating step is accomplished by electrophoresis.

9. A method of claim 7 wherein TcAK1 DNA labeled with a radioactive isotope and the detecting and quantifying are accomplished by autoradiography.

* * * * *

UNITED STATES PATENT AND TRADEMARK OFFICE
CERTIFICATE OF CORRECTION

PATENT NO. : 5,863,729

DATED : January 26, 1999

INVENTOR(S) : Piwnica-Worms

It is certified that error appears in the above-identified patent and that said Letters Patent is hereby corrected as shown below:

At col. 12, line 17, please delete "lane 2)." and replace with --lane 1).--

Signed and Sealed this

Thirteenth Day of July, 1999

Attest:

Attesting Officer

Q. TODD DICKINSON

Acting Commissioner of Patents and Trademarks

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 2698 base pairs (B) TYPE: nucleic acid
(C) STRANDEDNESS: double
(D) TOPOLOGY: Not Relevant (ii) MOLECULE TYPE: cDNA to mRNA (iii) HYPOTHETICAL: NO (iv) ANTI-SENSE: NO (ix) FEATURE:
    (A) NAME/KEY: CDS
    (B) LOCATION: 376..2565

(xi) SEQUENCE DESCRIPTION: SEQ ID NO:1:

```
GAGCTGAAAT TCGCGGTGCG ACGGGAGGGA GTGGAGAAGG AGGTGAGGGG GCCCAGGATC        60

GCGGGGCGCC CTGAGGCAAG GGGACGCCGG TGGGTCGAAG CGCAGCCCGC CGCCCGCAGG       120

CTCGGCTCCG CCACTGCCGC CCTCCCGGTC TCCTCGCCTC GGGCGCCGAG GCAGGGAGAG       180

AATGAGCCCC GGGACCCGCC GGGGACGGC  CCGGGCCAGG CCCGGGATCT AGAACGGCCG       240

TAGGGGAAG  GGAGCCGCCC TCCCCACGGC GCCTTTTCGG AACTGCCGTG GACTCGAGGA       300

CGCTGGTCGC CGGCCTCCTA GGGCTGTGCT GTTTTGTTTT GACCCTCGCA TTGTGCAGAA       360

TTAAAGTGCA GTAAA ATG TCC ACT AGG ACC CCA TTG CCA ACG GTG AAT GAA        411
                 Met Ser Thr Arg Thr Pro Leu Pro Thr Val Asn Glu
                  1               5                  10

CGA GAC ACT GAA AAC CAC ACG TCA CAT GGA GAT GGG CGT CAA GAA GTT        459
Arg Asp Thr Glu Asn His Thr Ser His Gly Asp Gly Arg Gln Glu Val
             15              20                  25

ACC TCT CGT ACC AGC CGC TCA GGA GCT CGG TGT AGA AAC TCT ATA GCC        507
Thr Ser Arg Thr Ser Arg Ser Gly Ala Arg Cys Arg Asn Ser Ile Ala
         30              35                  40

TCC TGT GCA GAT GAA CAA CCT CAC ATC GGA AAC TAC AGA CTG TTG AAA        555
Ser Cys Ala Asp Glu Gln Pro His Ile Gly Asn Tyr Arg Leu Leu Lys
 45              50                  55                      60

ACA ATC GGC AAG GGG AAT TTT GCA AAA GTA AAA TTG GCA AGA CAT ATC        603
Thr Ile Gly Lys Gly Asn Phe Ala Lys Val Lys Leu Ala Arg His Ile
             65                  70                      75

CTT ACA GGC AGA GAG GTT GCA ATA AAA ATA ATT GAC AAA ACT CAG TTG        651
Leu Thr Gly Arg Glu Val Ala Ile Lys Ile Ile Asp Lys Thr Gln Leu
             80                  85                      90

AAT CCA ACA AGT CTA CAA AAG CTC TTC AGA GAA GTA AGA ATA ATG AAG        699
Asn Pro Thr Ser Leu Gln Lys Leu Phe Arg Glu Val Arg Ile Met Lys
         95                 100                 105

ATT TTA AAT CAT CCC AAT ATA GTG AAG TTA TTC GAA GTC ATT GAA ACT        747
Ile Leu Asn His Pro Asn Ile Val Lys Leu Phe Glu Val Ile Glu Thr
    110                 115                     120

GAA AAA ACA CTC TAC CTA ATC ATG GAA TAT GCA AGT GGA GGT GAA GTA        795
Glu Lys Thr Leu Tyr Leu Ile Met Glu Tyr Ala Ser Gly Gly Glu Val
125             130                     135                 140

TTT GAC TAT TTG GTT GCA CAT GGC AGG ATG AAG GAA AAA GAA GCA AGA        843
Phe Asp Tyr Leu Val Ala His Gly Arg Met Lys Glu Lys Glu Ala Arg
                145                     150                 155

TCT AAA TTT AGA CAG ATT GTG TCT GCA GTT CAA TAC TGC CAT CAG AAA        891
Ser Lys Phe Arg Gln Ile Val Ser Ala Val Gln Tyr Cys His Gln Lys
            160                     165                 170

CGG ATC GTA CAT CGA GAC CTC AAG GCT GAA AAT CTA TTG TTA GAT GCC        939
Arg Ile Val His Arg Asp Leu Lys Ala Glu Asn Leu Leu Leu Asp Ala
            175                     180                 185

GAT ATG AAC ATT AAA ATA GCA GAT TTC GGT TTT AGC AAT GAA TTT ACT        987
Asp Met Asn Ile Lys Ile Ala Asp Phe Gly Phe Ser Asn Glu Phe Thr
    190                     195                 200
```

| | | | | | | | | | | | | | | | | |
|---|---|---|---|---|---|---|---|---|---|---|---|---|---|---|---|---|
| GTT | GGC | GGT | AAA | CTC | GAC | ACG | TTT | TGT | GGC | AGT | CCT | CCA | TAC | GCA | GCA | 1035 |
| Val | Gly | Gly | Lys | Leu | Asp | Thr | Phe | Cys | Gly | Ser | Pro | Pro | Tyr | Ala | Ala | |
| 205 | | | | 210 | | | | | 215 | | | | | | 220 | |
| CCT | GAG | CTC | TTC | CAG | GGC | AAG | AAA | TAT | GAC | GGG | CCA | GAA | GTG | GAT | GTG | 1083 |
| Pro | Glu | Leu | Phe | Gln | Gly | Lys | Lys | Tyr | Asp | Gly | Pro | Glu | Val | Asp | Val | |
| | | | | 225 | | | | 230 | | | | | 235 | | | |
| TGG | AGT | CTG | GGG | GTC | ATT | TTA | TAC | ACA | CTA | GTC | AGT | GGC | TCA | CTT | CCC | 1131 |
| Trp | Ser | Leu | Gly | Val | Ile | Leu | Tyr | Thr | Leu | Val | Ser | Gly | Ser | Leu | Pro | |
| | | | 240 | | | | | 245 | | | | | 250 | | | |
| TTT | GAT | GGG | CAA | AAC | CTA | AAG | GAA | CTG | AGA | GAG | AGA | GTA | TTA | AGA | GGG | 1179 |
| Phe | Asp | Gly | Gln | Asn | Leu | Lys | Glu | Leu | Arg | Glu | Arg | Val | Leu | Arg | Gly | |
| | | 255 | | | | | 260 | | | | | 265 | | | | |
| AAA | TAC | AGA | ATT | CCC | TTC | TAC | ATG | TCT | ACA | GAC | TGT | GAA | AAC | CTT | CTC | 1227 |
| Lys | Tyr | Arg | Ile | Pro | Phe | Tyr | Met | Ser | Thr | Asp | Cys | Glu | Asn | Leu | Leu | |
| | 270 | | | | | 275 | | | | | 280 | | | | | |
| AAA | CGT | TTC | CTG | GTG | CTA | AAT | CCA | ATT | AAA | CGC | GGC | ACT | CTA | GAG | CAA | 1275 |
| Lys | Arg | Phe | Leu | Val | Leu | Asn | Pro | Ile | Lys | Arg | Gly | Thr | Leu | Glu | Gln | |
| 285 | | | | | 290 | | | | | 295 | | | | | 300 | |
| ATC | ATG | AAG | GAC | AGG | TGG | ATC | AAT | GCA | GGG | CAT | GAA | GAA | GAT | GAA | CTC | 1323 |
| Ile | Met | Lys | Asp | Arg | Trp | Ile | Asn | Ala | Gly | His | Glu | Glu | Asp | Glu | Leu | |
| | | | | 305 | | | | | 310 | | | | | 315 | | |
| AAA | CCA | TTT | GTT | GAA | CCA | GAG | CTA | GAC | ATC | TCA | GAC | CAA | AAA | AGA | ATA | 1371 |
| Lys | Pro | Phe | Val | Glu | Pro | Glu | Leu | Asp | Ile | Ser | Asp | Gln | Lys | Arg | Ile | |
| | | | 320 | | | | | 325 | | | | | 330 | | | |
| GAT | ATT | ATG | GTG | GGA | ATG | GGA | TAT | TCA | CAA | GAA | GAA | ATT | CAA | GAA | TCT | 1419 |
| Asp | Ile | Met | Val | Gly | Met | Gly | Tyr | Ser | Gln | Glu | Glu | Ile | Gln | Glu | Ser | |
| | | 335 | | | | | 340 | | | | | 345 | | | | |
| CTT | AGT | AAG | ATG | AAA | TAC | GAT | GAA | ATC | ACA | GCT | ACA | TAT | TTG | TTA | TTG | 1467 |
| Leu | Ser | Lys | Met | Lys | Tyr | Asp | Glu | Ile | Thr | Ala | Thr | Tyr | Leu | Leu | Leu | |
| | 350 | | | | | 355 | | | | | 360 | | | | | |
| GGG | AGA | AAA | TCT | TCA | GAG | CTG | GAT | GCT | AGT | GAT | TCC | AGT | TCT | AGC | AGC | 1515 |
| Gly | Arg | Lys | Ser | Ser | Glu | Leu | Asp | Ala | Ser | Asp | Ser | Ser | Ser | Ser | Ser | |
| 365 | | | | | 370 | | | | | 375 | | | | | 380 | |
| AAT | CTT | TCA | CTT | GCT | AAG | GTT | AGG | CCG | AGC | AGT | GAT | CTC | AAC | AAC | AGT | 1563 |
| Asn | Leu | Ser | Leu | Ala | Lys | Val | Arg | Pro | Ser | Ser | Asp | Leu | Asn | Asn | Ser | |
| | | | | 385 | | | | | 390 | | | | | 395 | | |
| ACT | GGC | CAG | TCT | CCT | CAC | CAC | AAA | GTG | CAG | AGA | AGT | GTT | TCT | TCA | AGC | 1611 |
| Thr | Gly | Gln | Ser | Pro | His | His | Lys | Val | Gln | Arg | Ser | Val | Ser | Ser | Ser | |
| | | | | 400 | | | | | 405 | | | | | 410 | | |
| CAA | AAG | CAA | AGA | CGC | TAC | AGT | GAC | CAT | GCT | GGA | CCA | GCT | ATT | CCT | TCT | 1659 |
| Gln | Lys | Gln | Arg | Arg | Tyr | Ser | Asp | His | Ala | Gly | Pro | Ala | Ile | Pro | Ser | |
| | | 415 | | | | | 420 | | | | | 425 | | | | |
| GTT | GTG | GCG | TAT | CCG | AAA | AGG | AGT | CAG | ACA | AGC | ACT | GCA | GAT | GGT | GAC | 1707 |
| Val | Val | Ala | Tyr | Pro | Lys | Arg | Ser | Gln | Thr | Ser | Thr | Ala | Asp | Gly | Asp | |
| | | 430 | | | | 435 | | | | | 440 | | | | | |
| CTC | AAA | GAA | GAT | GGA | ATT | TCC | TCC | CGG | AAA | TCA | AGT | GGC | AGT | GCT | GTT | 1755 |
| Leu | Lys | Glu | Asp | Gly | Ile | Ser | Ser | Arg | Lys | Ser | Ser | Gly | Ser | Ala | Val | |
| 445 | | | | | 450 | | | | | 455 | | | | | 460 | |
| GGA | GGA | AAG | GGA | ATT | GCT | CCA | GCC | AGT | CCC | ATG | CTT | GGG | AAT | GCA | AGT | 1803 |
| Gly | Gly | Lys | Gly | Ile | Ala | Pro | Ala | Ser | Pro | Met | Leu | Gly | Asn | Ala | Ser | |
| | | | | 465 | | | | | 470 | | | | | 475 | | |
| AAT | CCT | AAT | AAG | GCG | GAT | ATT | CCT | GAA | CGC | AAG | AAA | AGC | TCC | ACT | GTC | 1851 |
| Asn | Pro | Asn | Lys | Ala | Asp | Ile | Pro | Glu | Arg | Lys | Lys | Ser | Ser | Thr | Val | |
| | | | 480 | | | | | 485 | | | | | 490 | | | |
| CCT | AGT | AGT | AAC | ACA | GCA | TCT | GGT | GGA | ATG | ACA | CGA | CGA | AAT | ACT | TAT | 1899 |
| Pro | Ser | Ser | Asn | Thr | Ala | Ser | Gly | Gly | Met | Thr | Arg | Arg | Asn | Thr | Tyr | |
| | | 495 | | | | | 500 | | | | | 505 | | | | |
| GTT | TGC | AGT | GAG | AGA | ACT | ACA | GCT | GAT | AGA | CAC | TCA | GTG | ATT | CAG | AAT | 1947 |
| Val | Cys | Ser | Glu | Arg | Thr | Thr | Ala | Asp | Arg | His | Ser | Val | Ile | Gln | Asn | |
| 510 | | | | | 515 | | | | | 520 | | | | | | |

| | | | | | | | | | | | | | | | | |
|---|---|---|---|---|---|---|---|---|---|---|---|---|---|---|---|---|
| GGC | AAA | GAA | AAC | AGC | ACT | ATT | CCT | GAT | CAG | AGA | ACT | CCA | GTT | GCT | TCA | 1995 |
| Gly | Lys | Glu | Asn | Ser | Thr | Ile | Pro | Asp | Gln | Arg | Thr | Pro | Val | Ala | Ser | |
| 525 | | | | 530 | | | | | 535 | | | | | | 540 | |
| ACA | CAC | AGT | ATC | AGT | AGT | GCA | GCC | ACC | CCA | GAT | CGA | ATC | CGC | TTC | CCA | 2043 |
| Thr | His | Ser | Ile | Ser | Ser | Ala | Ala | Thr | Pro | Asp | Arg | Ile | Arg | Phe | Pro | |
| | | | | 545 | | | | | 550 | | | | | 555 | | |
| AGA | GGC | ACT | GCC | AGT | CGT | AGC | ACT | TTC | CAC | GGC | CAG | CCC | CGG | GAA | CGG | 2091 |
| Arg | Gly | Thr | Ala | Ser | Arg | Ser | Thr | Phe | His | Gly | Gln | Pro | Arg | Glu | Arg | |
| | | | 560 | | | | | 565 | | | | | 570 | | | |
| CGA | ACC | GCA | ACA | TAT | AAT | GGC | CCT | CCT | GCC | TCT | CCC | AGC | CTG | TCC | CAT | 2139 |
| Arg | Thr | Ala | Thr | Tyr | Asn | Gly | Pro | Pro | Ala | Ser | Pro | Ser | Leu | Ser | His | |
| | | 575 | | | | | 580 | | | | | 585 | | | | |
| GAA | GCC | ACA | CCA | TTG | TCC | CAG | ACT | CGA | AGC | CGA | GGC | TCC | ACT | AAT | CTC | 2187 |
| Glu | Ala | Thr | Pro | Leu | Ser | Gln | Thr | Arg | Ser | Arg | Gly | Ser | Thr | Asn | Leu | |
| | 590 | | | | | 595 | | | | | 600 | | | | | |
| TTT | AGT | AAA | TTA | ACT | TCA | AAA | CTC | ACA | AGG | AGT | CGC | AAT | GTA | TCT | GCT | 2235 |
| Phe | Ser | Lys | Leu | Thr | Ser | Lys | Leu | Thr | Arg | Ser | Arg | Asn | Val | Ser | Ala | |
| 605 | | | | | 610 | | | | | 615 | | | | | 620 | |
| GAG | CAA | AAA | GAT | GAA | AAC | AAA | GAA | GCA | AAG | CCT | CGA | TCC | CTA | CGC | TTC | 2283 |
| Glu | Gln | Lys | Asp | Glu | Asn | Lys | Glu | Ala | Lys | Pro | Arg | Ser | Leu | Arg | Phe | |
| | | | | 625 | | | | | 630 | | | | | 635 | | |
| ACC | TGG | AGC | ATG | AAA | ACC | ACT | AGT | TCA | ATG | GAT | CCC | GGG | GAC | ATG | ATG | 2331 |
| Thr | Trp | Ser | Met | Lys | Thr | Thr | Ser | Ser | Met | Asp | Pro | Gly | Asp | Met | Met | |
| | | | 640 | | | | | 645 | | | | | 650 | | | |
| CGG | GAA | ATC | CGC | AAA | GTG | TTG | GAC | GCC | AAT | AAC | TGC | GAC | TAT | GAG | CAG | 2379 |
| Arg | Glu | Ile | Arg | Lys | Val | Leu | Asp | Ala | Asn | Asn | Cys | Asp | Tyr | Glu | Gln | |
| | | 655 | | | | | 660 | | | | | 665 | | | | |
| AGG | GAG | CGC | TTC | TTG | CTC | TTC | TGC | GTC | CAC | GGA | GAT | GGG | CAC | GCG | GAG | 2427 |
| Arg | Glu | Arg | Phe | Leu | Leu | Phe | Cys | Val | His | Gly | Asp | Gly | His | Ala | Glu | |
| | 670 | | | | | 675 | | | | | 680 | | | | | |
| AAC | CTC | GTG | CAG | TGG | GAA | ATG | GAA | GTG | TGC | AAG | CTG | CCA | AGA | CTG | TCT | 2475 |
| Asn | Leu | Val | Gln | Trp | Glu | Met | Glu | Val | Cys | Lys | Leu | Pro | Arg | Leu | Ser | |
| 685 | | | | | 690 | | | | | 695 | | | | | 700 | |
| CTG | AAC | GGG | GTC | CGG | TTT | AAG | CGG | ATA | TCG | GGG | ACA | TCC | ATA | GCC | TTC | 2523 |
| Leu | Asn | Gly | Val | Arg | Phe | Lys | Arg | Ile | Ser | Gly | Thr | Ser | Ile | Ala | Phe | |
| | | | | 705 | | | | | 710 | | | | | 715 | | |
| AAA | AAT | ATT | GCT | TCC | AAA | ATT | GCC | AAT | GAG | CTA | AAG | CTG | TAA | | | 2565 |
| Lys | Asn | Ile | Ala | Ser | Lys | Ile | Ala | Asn | Glu | Leu | Lys | Leu | * | | | |
| | | | 720 | | | | | 725 | | | | | 730 | | | |

CCCAGTGATT ATGATGTAAA TTAAGTAGCA AGTAAAGTGT TTTCCTGAAC ACTGATGGAA 2625

ATGTATAGAA TAATATTTAG GCAATAACGT CTGCATCTTC TAAATCATGA AATTAAAGTC 2685

TGAGGACGAG AGC 2698

( 2 ) INFORMATION FOR SEQ ID NO:2:

( i ) SEQUENCE CHARACTERISTICS:
        ( A ) LENGTH: 729 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Ser | Thr | Arg | Thr | Pro | Leu | Pro | Thr | Val | Asn | Glu | Arg | Asp | Thr | Glu |
| 1 | | | | 5 | | | | | 10 | | | | | 15 | |
| Asn | His | Thr | Ser | His | Gly | Asp | Gly | Arg | Gln | Glu | Val | Thr | Ser | Arg | Thr |
| | | | 20 | | | | | 25 | | | | | 30 | | |
| Ser | Arg | Ser | Gly | Ala | Arg | Cys | Arg | Asn | Ser | Ile | Ala | Ser | Cys | Ala | Asp |
| | | 35 | | | | | 40 | | | | | 45 | | | |
| Glu | Gln | Pro | His | Ile | Gly | Asn | Tyr | Arg | Leu | Leu | Lys | Thr | Ile | Gly | Lys |

-continued

```
               50                           55                           60
Gly  Asn  Phe  Ala  Lys  Val  Lys  Leu  Ala  Arg  His  Ile  Leu  Thr  Gly  Arg
 65                      70                           75                       80

Glu  Val  Ala  Ile  Lys  Ile  Ile  Asp  Lys  Thr  Gln  Leu  Asn  Pro  Thr  Ser
                     85                      90                           95

Leu  Gln  Lys  Leu  Phe  Arg  Glu  Val  Arg  Ile  Met  Lys  Ile  Leu  Asn  His
               100                      105                      110

Pro  Asn  Ile  Val  Lys  Leu  Phe  Glu  Val  Ile  Glu  Thr  Glu  Lys  Thr  Leu
          115                      120                      125

Tyr  Leu  Ile  Met  Glu  Tyr  Ala  Ser  Gly  Gly  Glu  Val  Phe  Asp  Tyr  Leu
     130                      135                      140

Val  Ala  His  Gly  Arg  Met  Lys  Glu  Lys  Glu  Ala  Arg  Ser  Lys  Phe  Arg
145                      150                      155                      160

Gln  Ile  Val  Ser  Ala  Val  Gln  Tyr  Cys  His  Gln  Lys  Arg  Ile  Val  His
                    165                      170                      175

Arg  Asp  Leu  Lys  Ala  Glu  Asn  Leu  Leu  Leu  Asp  Ala  Asp  Met  Asn  Ile
               180                      185                      190

Lys  Ile  Ala  Asp  Phe  Gly  Phe  Ser  Asn  Glu  Phe  Thr  Val  Gly  Gly  Lys
          195                      200                      205

Leu  Asp  Thr  Phe  Cys  Gly  Ser  Pro  Pro  Tyr  Ala  Ala  Pro  Glu  Leu  Phe
     210                      215                      220

Gln  Gly  Lys  Lys  Tyr  Asp  Gly  Pro  Glu  Val  Asp  Val  Trp  Ser  Leu  Gly
225                      230                      235                      240

Val  Ile  Leu  Tyr  Thr  Leu  Val  Ser  Gly  Ser  Leu  Pro  Phe  Asp  Gly  Gln
                    245                      250                      255

Asn  Leu  Lys  Glu  Leu  Arg  Glu  Arg  Val  Leu  Arg  Gly  Lys  Tyr  Arg  Ile
               260                      265                      270

Pro  Phe  Tyr  Met  Ser  Thr  Asp  Cys  Glu  Asn  Leu  Leu  Lys  Arg  Phe  Leu
          275                      280                      285

Val  Leu  Asn  Pro  Ile  Lys  Arg  Gly  Thr  Leu  Glu  Gln  Ile  Met  Lys  Asp
     290                      295                      300

Arg  Trp  Ile  Asn  Ala  Gly  His  Glu  Glu  Asp  Glu  Leu  Lys  Pro  Phe  Val
305                      310                      315                      320

Glu  Pro  Glu  Leu  Asp  Ile  Ser  Asp  Gln  Lys  Arg  Ile  Asp  Ile  Met  Val
                    325                      330                      335

Gly  Met  Gly  Tyr  Ser  Gln  Glu  Glu  Ile  Gln  Glu  Ser  Leu  Ser  Lys  Met
               340                      345                      350

Lys  Tyr  Asp  Glu  Ile  Thr  Ala  Thr  Tyr  Leu  Leu  Leu  Gly  Arg  Lys  Ser
          355                      360                      365

Ser  Glu  Leu  Asp  Ala  Ser  Asp  Ser  Ser  Ser  Ser  Asn  Leu  Ser  Leu
     370                      375                      380

Ala  Lys  Val  Arg  Pro  Ser  Ser  Asp  Leu  Asn  Asn  Ser  Thr  Gly  Gln  Ser
385                      390                      395                      400

Pro  His  His  Lys  Val  Gln  Arg  Ser  Val  Ser  Ser  Gln  Lys  Gln  Arg
                    405                      410                      415

Arg  Tyr  Ser  Asp  His  Ala  Gly  Pro  Ala  Ile  Pro  Ser  Val  Val  Ala  Tyr
               420                      425                      430

Pro  Lys  Arg  Ser  Gln  Thr  Ser  Thr  Ala  Asp  Gly  Asp  Leu  Lys  Glu  Asp
          435                      440                      445

Gly  Ile  Ser  Ser  Arg  Lys  Ser  Ser  Gly  Ser  Ala  Val  Gly  Gly  Lys  Gly
     450                      455                      460

Ile  Ala  Pro  Ala  Ser  Pro  Met  Leu  Gly  Asn  Ala  Ser  Asn  Pro  Asn  Lys
465                      470                      475                      480
```

```
Ala Asp Ile Pro Glu Arg Lys Lys Ser Ser Thr Val Pro Ser Ser Asn
            485                 490                 495
Thr Ala Ser Gly Gly Met Thr Arg Arg Asn Thr Tyr Val Cys Ser Glu
            500                 505                 510
Arg Thr Thr Ala Asp Arg His Ser Val Ile Gln Asn Gly Lys Glu Asn
        515                 520                 525
Ser Thr Ile Pro Asp Gln Arg Thr Pro Val Ala Ser Thr His Ser Ile
        530                 535                 540
Ser Ser Ala Ala Thr Pro Asp Arg Ile Arg Phe Pro Arg Gly Thr Ala
545                 550                 555                 560
Ser Arg Ser Thr Phe His Gly Gln Pro Arg Glu Arg Arg Thr Ala Thr
                565                 570                 575
Tyr Asn Gly Pro Pro Ala Ser Pro Ser Leu Ser His Glu Ala Thr Pro
            580                 585                 590
Leu Ser Gln Thr Arg Ser Arg Gly Ser Thr Asn Leu Phe Ser Lys Leu
            595                 600                 605
Thr Ser Lys Leu Thr Arg Ser Arg Asn Val Ser Ala Glu Gln Lys Asp
    610                 615                 620
Glu Asn Lys Glu Ala Lys Pro Arg Ser Leu Arg Phe Thr Trp Ser Met
625                 630                 635                 640
Lys Thr Thr Ser Ser Met Asp Pro Gly Asp Met Met Arg Glu Ile Arg
                645                 650                 655
Lys Val Leu Asp Ala Asn Asn Cys Asp Tyr Glu Gln Arg Glu Arg Phe
            660                 665                 670
Leu Leu Phe Cys Val His Gly Asp Gly His Ala Glu Asn Leu Val Gln
            675                 680                 685
Trp Glu Met Glu Val Cys Lys Leu Pro Arg Leu Ser Leu Asn Gly Val
        690                 695                 700
Arg Phe Lys Arg Ile Ser Gly Thr Ser Ile Ala Phe Lys Asn Ile Ala
705                 710                 715                 720
Ser Lys Ile Ala Asn Glu Leu Lys Leu
                725                 730
```

( 2 ) INFORMATION FOR SEQ ID NO:3:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:3:

```
Glu Gln Pro His Ile Gly Asn Tyr Arg Leu Leu Lys Thr Ile Gly Lys
 1               5                  10                  15
Gly Asn Phe Ala Lys Val Lys Leu Ala
            20                  25
```

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: Not Relevant 5,863,729

( i i ) MOLECULE TYPE: protein ( i i i ) HYPOTHETICAL: NO ( v ) FRAGMENT TYPE: internal ( x i ) SEQUENCE DESCRIPTION: SEQ ID NO:4:

```
Tyr  Arg  Ser  Pro  Ser  Met  Pro  Glu  Asn  Leu  Asn  Arg  Pro  Arg  Leu  Lys
 1              5                        10                       15
```

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide for
            site- directed mutagenesis"

( i i i ) HYPOTHETICAL: NO ( i v ) ANTI-SENSE: NO ( x i ) SEQUENCE DESCRIPTION: SEQ ID NO:5:

ATATCGCTCC CCGGCGATGC CAGAGAACTT 30

( 2 ) INFORMATION FOR SEQ ID NO:6:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide primer"

( i i i ) HYPOTHETICAL: NO ( x i ) SEQUENCE DESCRIPTION: SEQ ID NO:6:

CAGCATAAGC TTACCATGGC AGAACAGAAG CTCATTTCTG AAGAAGACTT GTCTACGGAA 60

CTCTTCTCA 69

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide primer"

( i i i ) HYPOTHETICAL: NO ( x i ) SEQUENCE DESCRIPTION: SEQ ID NO:7:

AATGCACTTC CTGAAGTCCT GAAGA 25

( 2 ) INFORMATION FOR SEQ ID NO:8:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: other nucleic acid ( A ) DESCRIPTION: /desc ="Oligonucleotide primer"

( i i i ) HYPOTHETICAL: NO ( x i ) SEQUENCE DESCRIPTION: SEQ ID NO:8:

TCGAGGTACC                                                                                                              10

( 2 ) INFORMATION FOR SEQ ID NO:9:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide primer"

( i i i ) HYPOTHETICAL: NO ( x i ) SEQUENCE DESCRIPTION: SEQ ID NO:9:

CGTGTTCCAC TCTGAATTCT CCTCAGAGAG GGGCCCCGG ATGTGCCGC                                                                     49

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide primer"

( i i i ) HYPOTHETICAL: NO ( x i ) SEQUENCE DESCRIPTION: SEQ ID NO:10:

CGAGTCATAT GTCCACTAGG ACCCC                                                                                              25

( 2 ) INFORMATION FOR SEQ ID NO:11:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide primer"

( i i i ) HYPOTHETICAL: NO ( x i ) SEQUENCE DESCRIPTION: SEQ ID NO:11:

CCAGTCATAT GTTAACTTAC AGCTTTAGCT CATTTGGC                                                                                38

( 2 ) INFORMATION FOR SEQ ID NO:12:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide primer"

( i i i ) HYPOTHETICAL: NO ( x i ) SEQUENCE DESCRIPTION: SEQ ID NO:12:

CCAGTCATAT GTTAACTTAG CTTGAAGAAA CACTTCTCTG C                                                                            41

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide primer"

( i i i ) HYPOTHETICAL: NO ( x i ) SEQUENCE DESCRIPTION: SEQ ID NO:13:

CAAGGCTGAA GCTCTATTGT TAGATGC    27

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Oligonucleotide primer"

( i i i ) HYPOTHETICAL: NO ( x i ) SEQUENCE DESCRIPTION: SEQ ID NO:14:

GCATCTAACA ATAGAGCTTC AGCCTTG    27

( 2 ) INFORMATION FOR SEQ ID NO:15:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: Not Relevant ( i i ) MOLECULE TYPE: protein ( i i i ) HYPOTHETICAL: NO ( v ) FRAGMENT TYPE: C-terminal ( x i ) SEQUENCE DESCRIPTION: SEQ ID NO:15:

Lys  Asn  Ile  Ala  Ser  Lys  Ile  Ala  Asn  Glu  Leu  Lys  Leu
   1                    5                        10

( 2 ) INFORMATION FOR SEQ ID NO:16:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: Not Relevant ( i i ) MOLECULE TYPE: protein ( i i i ) HYPOTHETICAL: NO ( v ) FRAGMENT TYPE: internal ( x i ) SEQUENCE DESCRIPTION: SEQ ID NO:16:

Lys  Gln  Lys  Asp  Glu  Asn  Lys  Glu  Ala  Lys  Pro  Arg  Ser
   1                    5                        10

( 2 ) INFORMATION FOR SEQ ID NO:17:

( i ) SEQUENCE CHARACTERISTICS:

( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: internal ( x i ) SEQUENCE DESCRIPTION: SEQ ID NO:17:

Glu  Gln  Lys  Leu  Ile  Ser  Glu  Glu  Asp  Leu
    1              5                        10